United States Patent [19]
Yager et al.

[11] Patent Number: 5,851,536
[45] Date of Patent: Dec. 22, 1998

[54] THERAPEUTIC DELIVERY USING COMPOUNDS SELF-ASSEMBLED INTO HIGH AXIAL RATIO MICROSTRUCTURES

[75] Inventors: Paul Yager; Michael H. Gelb; Paul A. Carlson; Kyujin C. Lee; Anatoly N. Lukyanov; Alex S. Goldstein, all of Seattle, Wash.

[73] Assignee: University of Washington, Seattle, Wash.

[21] Appl. No.: 752,848

[22] Filed: Nov. 21, 1996

Related U.S. Application Data

[60] Provisional application No. 60/025,137, Nov. 22, 1995.
[51] Int. Cl.[6] .............................. A61K 9/00; A61K 9/127
[52] U.S. Cl. .............................................. 424/400; 424/450
[58] Field of Search ..................... 424/400, 450, 424/443; 428/357, 221

[56] References Cited

U.S. PATENT DOCUMENTS

| | | | |
|---|---|---|---|
| 4,871,488 | 10/1989 | Mannino | 264/4.6 |
| 4,990,291 | 2/1991 | Schoen | 264/4.7 |
| 5,643,574 | 7/1997 | Gould-Fogerite | 424/184.1 |

OTHER PUBLICATIONS

Tovchilin in BBRC. 85, #3, pp. 983–990, Dec. 1978.

*Primary Examiner*—Gollamudi S. Kishore
*Attorney, Agent, or Firm*—Klarquist Sparkman Campbell Leigh & Whinston, LLP

[57] ABSTRACT

Therapeutic agents comprising plural therapeutic compounds self assembled into high axial ratio microstructures are described. The threapeutic compounds satisfy the formula HARFM-Th, wherein HARFM is a high axial ratio forming material and Th is a therapeutic associated with the HARFM. The therapeutic agent also can satisfy the formula HARFM-S-Th, wherein S is a spacer. Release of the therapeutic by the agent generally follows either 0-order kinetics or psuedofirst order kinetics. A method for delivering drugs to animals or persons also is described. The method comprises administering an effective amount of a therapeutic self-assembled into an HAR microstructure to the animal or person.

10 Claims, 7 Drawing Sheets

DRUG MOEITY

LINKER (IF REQUIRED)

CHIRAL HEADGROUP

HYDROCARBON CHAINS

THERAPEUTIC DELIVERY USING COMPOUNDS SELF-ASSEMBLED INTO HIGH AXIAL RATIO MICROSTRUCTURES

CROSS REFERENCE TO RELATED APPLICATION

This application claims priority from copending U.S. provisional patent application, No. 60/025,137, filed on Nov. 22, 1995, which is incorporated herein by reference.

FIELD OF THE INVENTION

The present invention concerns compounds, compositions and methods useful for delivering therapeutics.

BACKGROUND OF THE INVENTION

Two current issues in drug delivery concern the spatial and temporal attributes of therapeutic delivery systems. Targeting the therapeutic to limit its exposure to the desired site of action is the spatial aspect. Controlling the delivery of the therapeutic over time is the temporal aspect. Continuous drug release often is preferable to periodically administering bolus doses to the entire organism. Bolus administration results in a spike of drug concentration, followed by a decrease in concentration to baseline.

Moreover, patients often fail to comply with bolus drug administration procedures, one example being outpatients who do not complete their course of antibiotics. This is a key problem in controlling emerging drug-resistant strains of tuberculosis, and is probably a factor contributing to an increase in the appearance of many other drug-resistant strains of bacteria. The cost in morbidity and mortality from inadequate frequency of dosing with insulin is known to be in the billions of dollars in the United States alone. Reach et al.'s *Can Continuous Glucose Monitoring be used for the Treatment of Diabetes*, 64:381A–386A (Analytical Chemistry, 1992). Restricting ambulatory patients to a hospital setting to insure compliance (or establishing some other system of enforced compliance) is not a practical solution. Patient noncompliance with bolus administration procedures therefore is an important impetus for developing continuous drug delivery systems.

At present there are several approaches to controlled or continuous drug delivery, some of which are still in the research phases, and some of which have been successfully used in commercial products for some time. Prevost et al.'s *New Methods of Drug Delivery*, 249:1527–1533 (Science, 1990). The delivery approaches include: (1) external delivery systems, such as external mechanical pumps and osmotic patches; (2) internal osmotic pumps; and (3) implantable or ingestible polymeric structures that can include erodible hydrogels. With pumps, continuous release can be set by the pump design or by controlling the motor. Continuous drug delivery using continuous infusion with an i.v. line (the only viable method for some chemotherapeutic drugs) is costly and restricts the patient's movement. Implanted catheters and pumps are an expensive solution, the considerable risk of which is only balanced by the importance of continuous delivery of the drug in question. Using implantable macroscopic devices for drug delivery restricts the site of delivery to one that can accommodate the object. The NORPLANT® contraceptive system, effective though it is, requires a large insertion site and must be surgically recovered after use.

With polymeric structures the rate of delivery can be controlled by the shape and permeability-erodibility of the polymer. Dermal patches are very simple and relatively noninvasive. However, dermal patches have been effective only for a few drugs that are relatively permeant through the skin.

Some of the approaches discussed above work well for some classes of drugs, and are inapplicable to others The chemically labile nature of peptide drugs, for example, results in their incompatibility with many polymeric delivery systems. Those polymers in which they can be immobilized have yet to be approved for general use. And, the common feature of all the existing delivery systems listed above is that they control diffusion or effusion by a macroscopic mechanical object. This limits their usefulness and makes using the delivery systems a nuisance and perhaps even requires invasive surgical implanting.

Drug distribution can be controlled by the microstructures into which the drug self-assembles. Liposomes are one example of a self-assembled microstructure, and encapsulating drugs in liposomes has proven useful in some circumstances. Ostro, *Liposomes: From Biophysics to Therapeutics*, Marcel Dekker, Inc. (1987). For instance, liposomes can be used to deliver drugs to skin. Yager et al's *Conjugation of Phosphatidyl-ethanolamine to poly(n-isopropylacrylamide) for Potential Use in Liposomal Drug Delivery Systems*, 33:4659–4662 (Polymer, 1992). Phosphatidylglycerols have been modified with a wide range of peptide and non-peptide drugs (in particular AZT) with the assumption that they would self-assemble into liposomes, and would be trapped by macrophages in the reticuloendothelial system after injection into the bloodstream. Wang et al.'s *Synthesis of Phospholipid-Inhibitor Conjugates by Enzymatic Transphospha-tidylations with Phospholipase D*, 115:10487–10491 (J. Am. Chem. Soc., 1993). Beyond the general assumption that liposomes would be formed, how hydrophobically modified drugs self-associate, and how the self-association affects the conformation of the drugs themselves, is largely unknown.

Lipid tubules are a recently discovered self-organizing system in which lipids crystallize into tightly packed bilayers that spontaneously form hollow cylinders less than 1 $\mu$m in diameter. The basic subunit the tubule is a helical ribbon of lipid bilayer and, in some cases, open helical structures of the same diameter can be seen. In 1983, polymerizable diacetylenic phosphatidylcholines such as 1,2-di-(10,12-tricosadiynoyl)-sn-glycero3-phosphocholine (referred to as $DC_{8,9}PC$) were discovered by Yager and Schoen to form novel hollow tubular microstructures. See, for instance, Yager et al.'s *Formation of Tubules by a Polymerizable Surfactant*, 106:371–381 (Mol. Cryst. Liq. Cryst., 1984). Diacetylenic lipid tubules are straight, rigid, about 0.75 $\mu$m in diameter, and can be made to range in length from a few $\mu$m to nearly 1 mm, depending on the conditions used to form the microstructure. Further, the walls of the tubules may be as thin as a single bilayer. The lumen (the open space in a tubular organ or device) is generally open, allowing free access by diffusion from the ends of the microstructures.

Kunitake et al. demonstrated that a positively charged chiral amphiphile based on glutamate forms structures similar to those formed by $DC_{8,9}PC$. Kunitake et al.'s *Helical Superstructures are Formed from Chiral Ammonium Bilayer Membranes*, 1709–1712 (Chem. Lett., 1984). Helices and tubules of much smaller diameters (~300 Å) were found by Yamada et al. to form from related synthetic two-chain amphiphiles with oligopeptides (such as 12–14-mers of glutamic and aspartic acid) as hydrophilic headgroups. Yamada et al.'s *Formation of Helical Super Structure from Single-Walled Bilayers by Amphiphiles with Oligo-L-*

*Glutamic Acid-Head Group*, 10:1713–1716 (Chem. Lett., 1984). Yamada et al.'s *Amphiphiles with Polypeptide head Groups. 7. Relationship Between Formation of Helical Bilayer membranes and Chemical Structures of Dialkyl Amphiphiles with Polypeptide-Head Groups*, 48:327–334 (Kobunshi Ronbunshu, 1991). Recent work by Shimizu and Hato on similar lipids with polypeptide headgroups, including (Pro)$_3$-tripeptide, produced similar tubules and helices. Later studies by the Yamada group ascertained that both positive, negative and neutral amino acids could be incorporated into block copolymers as headgroups for glutamate-based lipopeptides.

However, fully charging the headgroups prevented tubule and helix formation. This is presumably because charging the polypeptide side chains increases the headgroup excluded volume to the point that close packing of the hydrocarbon chains is no longer possible in a planar bilayer. Further, there was evidence that the secondary structure of the polypeptide varied with the nature of the microstructure and that β-sheet formed between headgroup polypeptides.

It recently was determined that helical and tubular structures, as well as rod-like cochleate cylinders, can be formed quantitatively from the n-fatty acyl and α-hydroxy fatty acyl fractions of bovine brain galactocerebrosides, designated NFA-cer and HFA-cer, respectively. Yager et al.'s *Microstructural Polymorphism in Bovine Brain Galactocerebrosides and its Two Major Subfractions*, 31:9045–9055 (Biochem., 1992). Tubular and helical structures have now been observed in samples of aged suspensions of saturated-chain phosphatidylcholines and as transient intermediates in the crystallization of cholesterol from mixed micellar suspensions. See, for instance, Konikoff et al.'s *Filamentous, Helical, and Tubular Microstructures During Cholesterol Crystallization from Bile*, 90:1155–1160 (J. Clin. Invest., 1992).

There appear to have been no commercialized uses for tubules to date. Lipid tubules have been "decorated" with inorganic materials, including metals [See, for instance, Schnur et al.'s U.S. Pat. No. 4,911,981, entitled *Metal Clad Lipid Microstructures*] and salts [Yager et al.'s *Formation of Mineral Microstructures with a High Aspect Ratio from Phospholipid Bilayer Tubules*, 11:633–636 (J. Mat. Sci. Lett., 1992), although a practical use for these materials has not yet been reported. Some preliminary work has been undertaken to use the lumen of diacetylenic lipid tubules as a reservoir for the encapsulation of drugs for delivery in wound dressings. See, for instance, Cliff et al.'s *The Use of Lipid Microcylinders as Release Vehicles; Release Rates of Growth Factors and Cytokines*, Fourth World Biomaterials Conference (1992). These procedures have yet to realize and exploit the beneficial physical characteristics of tubules.

There also are patented approaches to using cochleate cylinders as drug delivery systems. For example, Mannino et al. have used cochleate cylinders, formed by the addition of calcium ions to some negatively charged phopholipids, to encapsulate materials. See, for example, U.S. Pat. Nos. 4,663,161 and 4,871,488, and international patent application, No. PCT/US96/01704. Mannino's cochleate cylinders apparently undergo a transformation to a liposomal intermediate prior to drug release.

SUMMARY OF THE INVENTION

The drug delivery approach described herein is distinctly different, and potentially much more widely applicable, than any of the prior known methods for continuously delivering therapeutics. The invention provides therapeutic materials which are themselves capable of forming high axial ratio microstructures, particularly tubules, cochleate cylinders, helical ribbons and twisted ribbons. Alternatively, compounds according to the formula $$HARFM\text{-}Th$$

are provided wherein "HARFM" comprises high axial ratio forming molecules, i.e., lipid molecules that are capable of self-assembling into such microstructures, and "Th" is a therapeutic covalently or otherwise coupled to the HARFM. The therapeutic can be any agent now known or hereafter developed that does not interfere with the formation of high axial ratio (HAR) microstructures. By way of example, and without limitation, the Th may be selected from the group consisting of peptides, nucleic acids, antigens and conventional pharmaceuticals.

Certain HARFMs further satisfy the formula $$R_1R_2CH\text{-}X$$

wherein $R_1$ and $R_2$ are alkyl, alkenyl (i.e., compounds that include at least one double bond), alkynyl (i.e., compounds that include at least one triple bond) or heteroalkyl, heteroalkenyl or heteroalkynyl chains having from about 10 to about 25 carbon atoms. Heteroalkyl, heteroalkenyl and heteroalkynyl compounds are compounds that include heteroatoms, such as, without limitation, nitrogen, oxygen and sulfur. X is a hydrophilic group. $R_1$ and $R_2$ preferably include at least one site of unsaturation, and generally are coupled to the carbon atom by functional groups that include heteroatoms, particularly but not necessarily, esters and amides. $R_1$ and $R_2$ also can be attached to a chiral carbon. Certain compounds according to this formula have been made wherein X is a polypeptide, such as polyglutamate or polyaspartate.

Moreover, spacers can be used to couple therapeutics to HARFMs. One example, without limitation, of a class of suitable spacers are polypeptides that include enzyme cleavage sites, such as protease cleavage sites recognized by trypsin, trypsin-like enzymes and elastase.

Still another embodiment of the invention provides HARFM-Ths which generally satisfy the formula $$R_1R_2\text{-}Y\text{-}CH\text{-}Th$$

wherein $R_1$ and $R_2$ are hydrophobic alkyl, alkenyl or alkynyl chains having from about 10 to about 25 carbon atoms, Y is selected from the group consisting of —CO—NH—, —NH—CO—, —O—CO—, and —CO—O—, and wherein Th is selected from the group consisting of peptides, nucleic acids antigens and conventional pharmaceuticals. $R_1$ and $R_2$ may both include at least one site of unsaturation.

The present invention also provides compositions useful for delivering therapeutic agents. The compositions comprise plural constituent molecules self-assembled into HAR microstructures. Each constituent molecule satisfies the formula $$HARFM\text{-}Th$$

as discussed above. The therapeutic may be coupled to the HARFM using a spacer (S), i.e. HARFM-S-Th.

The compositions may self assemble so that only a portion of the plural constituent molecules have therapeutics coupled to HARFMs. Moreover, the plural constituent molecules self-assembled into HAR microstructures can have plural different therapeutics. The result is a microstructure having plural different therapeutics associated therewith.

The present invention also provides a method for delivering therapeutic agents, particularly in a steady, continuous manner. The method comprises administering to a person or animal effective amounts of compounds or compositions made in accordance with the present invention comprising plural constituent molecules self-assembled into HAR microstructures. The method can comprise administering effective amounts of compounds satisfying the formulas discussed above, including the use of spacers. The compounds or compositions may be administered by any number of methods including, but not limited to, topically, orally, such as in the case of vaccines, intramuscularly, intranasally, subcutaneously, intraperitoneally, intralesionally or intravenously. And, the compositions may further comprise conventional materials known in the pharmaceutical field, including materials selected from the group consisting of aqueous buffers, stabilizers, diluents and adjuvants.

An object of the invention is to develop a device-free method by which drugs can be released into the body, particularly in a continuous manner (0-order kinetics) through association with HARFMS.

Another object of this invention is to form compounds and compositions comprising drugs or prodrugs associated with HARFMs that continuously release drugs either through dissolution of the molecules from the ends of the microstructures or through enzymatic cleavage.

Still another object of the present invention concerns using a homogeneous population of HARFMs to dissolve (or be enzymatically degraded) in such a manner that the rate of release of the constituent molecules (or parts thereof) is constant until the microstructures are consumed.

Still another object of the present invention is to ligate an appropriate hydrophobic anchoring moiety to water-soluble molecules and clinically significant therapeutics, such as conventional pharmaceuticals and bioactive polypeptides, and to allow such compounds to self-associate into HAR microstructures.

Still another object of the present invention is to provide compounds and compositions comprising therapeutics coupled to HARFMs by spacers. A particularly suitable class of spacers are peptides or polypeptides (polypeptides are defined herein to mean an amino acid chain having at least two amino acids linked by amide bonds). Such spacers also can include enzyme recognition sites.

Still another object of the present invention is to provide materials and methods useful for oral delivery of materials to the gut, such as delivery of therapeutics and vaccines to the small intestine, wherein such materials are generally impervious to the low pH and proteolytic activity of the stomach.

DETAILED DESCRIPTION OF THE PREFERRED EMBODIMENTS

Figure 1:
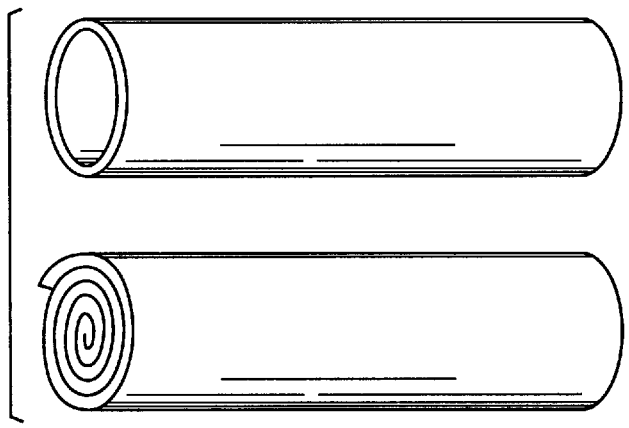
FIG. 1 is a schematic drawing illustrating non-liposomal microstructures of bilayer-forming amphiphiles.

The present invention provides therapeutic compounds and compositions comprising such therapeutics wherein such compounds are themselves capable of self assembling into HAR microstructures. As used herein, "HAR microstructure" refers to microstructures wherein the ratio of the major axes is from about 2 to 5,000, and more typically from about 2 to 1,000. For example, with an HFA-cerebroside cochleate cylinder having a diameter of about 0.1 μm, there are about 20 lipid bilayer "wraps" in the structure. This means that at the end of the cochleate cylinder there is about 3 μm of linear bilayer edge exposed. This cochleate cylinder would have an axial ratio of greater than 300 (30 μm in length divided by 0.1 μm in diameter=300). Examples, without limitation, of suitable HAR microstructures include tubules, cochleate cylinders, helical ribbons, twisted ribbons, and mixtures thereof. FIG. 1 provides a schematic representation of tubules and cochleate microstructures.

Alternatively, the therapeutic compounds may be coupled to materials capable of forming HAR microstructures, one example being covalently bonding therapeutic compounds to lipids capable of self assembling into HAR microstructures. Noncovalent attachment also may be used to associate the therapeutics with the lipids. The lipid components generally are, or are similar to, ceramides, phosphatidylcholines, amino acids and fatty acids; the structural components are generally intended to be completely metabolized into nontoxic products.

HARFMs solve many continuous drug delivery problems, and are useful for the continuous release of drugs. One reason for this is that the geometry of drug particles affects the kinetics of drug release. Moreover, the environment in which the compounds undergo hydrolysis or enzymatic cleavage also can effect the kinetics of the reaction. This is discussed in more detail below.

Figure 2:
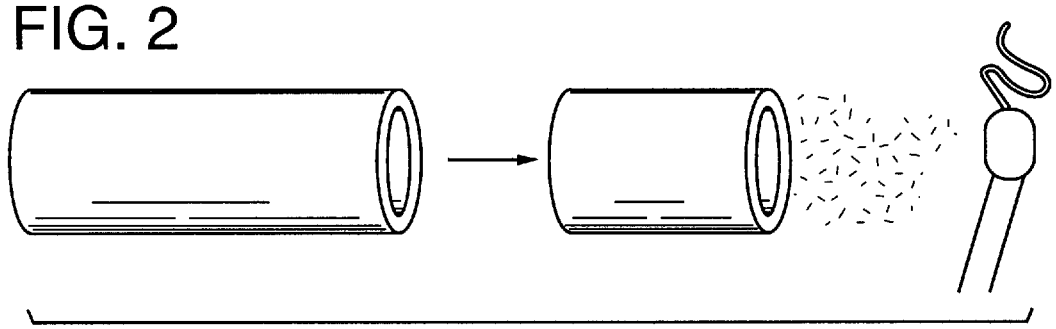
FIG. 2 is a schematic representation illustrating the dissolution of a therapeutic drug from the ends of a cylindrical microstructure.
Figure 3:
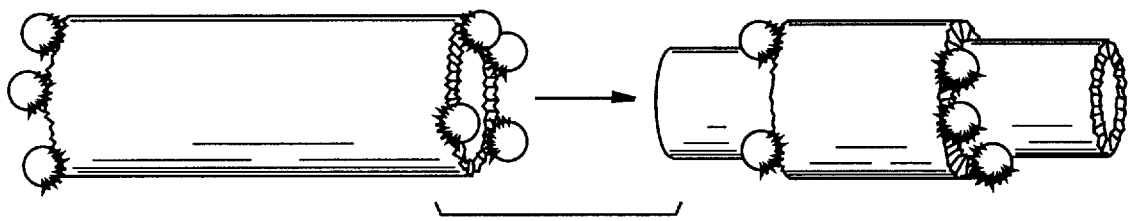
FIG. 3 is a schematic representation illustrating therapeutic release from a cylindrical microstructure under the influence of an enzyme-catalyzed hydrolysis reaction.

There are at least two methods for using HAR microstructures to produce continuous release of drugs. The first depends only on the dissolution of the drug from the ends of HAR microstructures. This mechanism is illustrated in FIG. 2. In the second mechanism, the drug is released from the HAR microstructure the influence of an enzyme-catalyzed hydrolysis reaction. This is illustrated in FIG. 3. See the "Kinetics" section below for more discussion.

The physical size of the HAR microstructures could prevent them from being used in all applications. However, a suspension of HAR microstructures should be usable in all circumstances for which macroscopic polymeric drug delivery systems are currently contemplated. This method of controlled release avoids pumps or incorporation of drug into a macroscopic rigid matrix of a particular shape. The small diameter of HAR microstructures allows them to be placed into cavities in the body using a needle or catheter, whereas their great length will immobilize them after injection. For example, a wide range of HARM-based antitumor drugs could be injected into tumors (intralesionally) using small needles, perhaps avoiding the need for major surgery in some cases.

The following paragraphs discuss the compounds and compositions of the present invention, provide detail concerning how such compounds can be made, as well as the kinetics of dissolution and enzymatic cleavage. Moreover, information concerning how to use the HAR microstructures for administering therapeutics also is provided.

HARFMs might themselves be useful therapeutics. Alternatively, therapeutics will be attached, such as by covalent bonding, to HARFMs to produce composite compounds according to the formulas HARFM-Th or HARFM-S-Th, wherein "HARFM" stands for high axial ratio forming molecules, "Th" is a therapeutic, and "S" is a spacer. Both the HARFM-Th and HARFM-S-Th compounds form suitable microstructures when subjected to microstructure-forming regimens. HARFMs, therapeutics and spacers each will be discussed separately below.

A. HARFMs

There are a number of HARFMs currently known, and these HARFMs likely can be used for the synthesis of composite (i.e., HARFM-Th; HARFM-S-Th) compounds. Other compounds also are capable of forming HAR microstructures. By way of example only and without limitation, the HARFMs currently deemed preferable for use in producing composite compounds for the delivery of therapeutics will be glutamate-based amphiphiles (Formula 1), polyglutamate-based amphiphiles (Formula 2), phosphatidylcholine with tricosadiynoyl fatty acyl chains, referred to as $DC_{8,9}PC$ (Formula 3), NFA-Gal-cer (Formula 4), and derivatives of these compounds. For example, NFA-Gal-cer can have an hydroxyl group $\alpha$ to the amide bond (this compound is referred to as HFA-Gal-Cer).

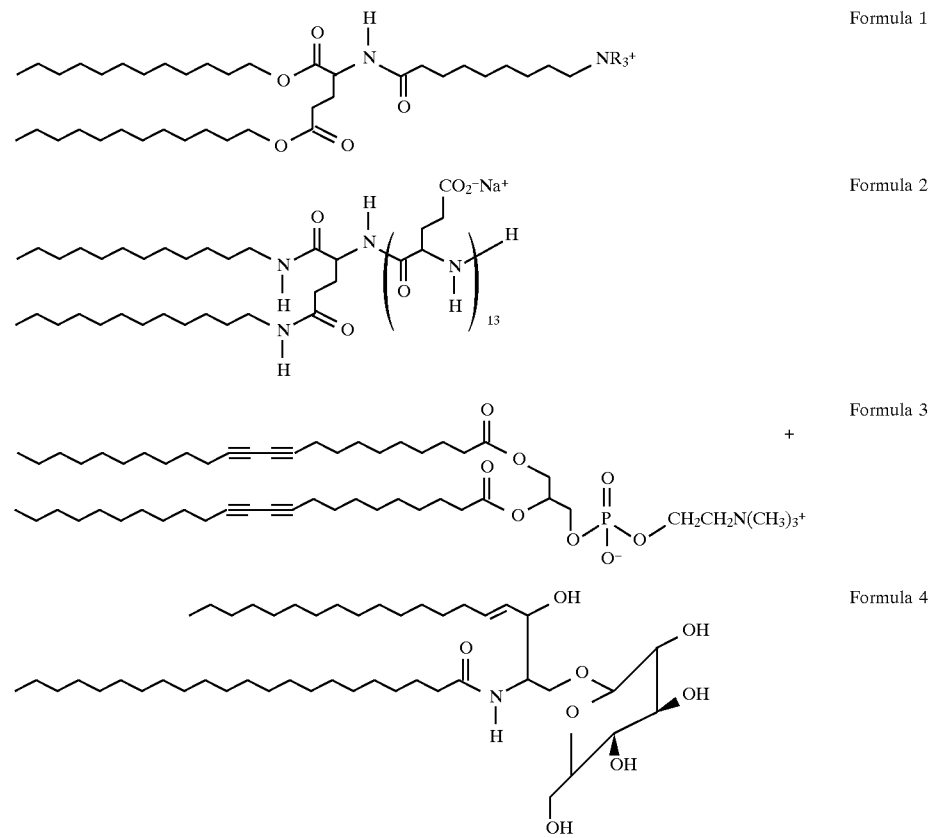

I. DESCRIPTION OF COMPOUNDS AND THEIR SYNTHESIS

The present compounds and compositions comprise HARFMs having therapeutics associated therewith.

The compounds represented by Formulas 1–4 can be synthesized according to published procedures or are commercially available. More specifically, $DC_{8,9}PC$ is commercially available from Avanti Polar Lipids, Birmingham AL, and NFA-Gal-cer and HFA-Gal-cer are commercially available from Sigma Chemical Company.

Glutamate-based amphiphiles (represented by Formula 1) can be synthesized using procedures published by Kunitake. See, for instance, Kunitake et al.'s *Helical Superstructures are Formed from Chiral Ammonium Bilayers*, 1709–1712 (Chem. Lett., 1984).

Compounds according to Formula 2, and derivatives thereof, can be synthesized according to the methods described by Yamada, such as in Yamada et al.'s *Formation of Helical Super Structure from Single-Walled Bilayers by Amphiphiles with Oligo-L-Glutamic Acid-Head Group*, 10:1713–1716 (Chem. Lett., 1984). Briefly, hexadecylamine was coupled to both of the free carboxyl groups of N-carbobenzoxy-L-glutamic acid with diethyl cyanophosphonate in the presence of triethylamine to form amide linkages. The carbobenzoxy protecting group was removed by hydrogenation using 10% Pd on activated carbon.

The compounds shown in Formulas 1–4 also can be modified to form additional compounds useful for forming HAR microstructures. For instance, the alkyl chains in each of the compounds shown in Formulas 1–4 can be changed to have different numbers of carbon atoms, as long as these modifications do not prevent such compounds from forming HAR microstructures under the appropriate conditions. For instance, the alkyl chain lengths for the compound of Formula 2 have been varied to be C-12, C-14 or C-16 (see compounds of Table 1 below) and these compounds appear to form HARFMs in accordance with the present invention.

TABLE 1

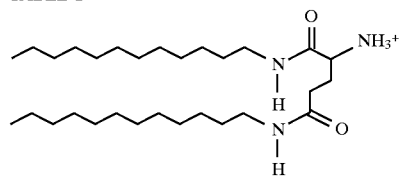

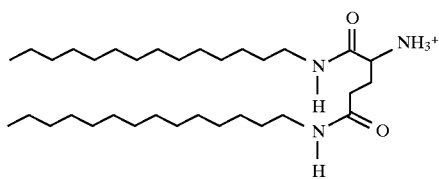

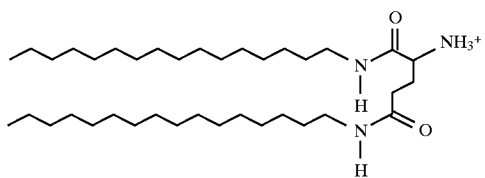

Moreover, compounds have been made using the core structures illustrated in Table 1 by attaching various amino acids, or polypeptides, to the amine nitrogen. These compounds are illustrated below, wherein the amino acids are represented by their familiar three-letter code. Compounds having plural proline amino acids, such as three proline groups, form cylindrical microstructures facilely. These compounds were made according to the procedure of Shimizu et al. See, for example, *Biochemica et Biophysica Acta.*, 1147: 50–58 (1993). And, compounds having polypeptides attached thereto were synthesized to include trypsin cleavage sites. The synthesis of compounds having amino acids attached thereto is described below in Examples 2 and 3.

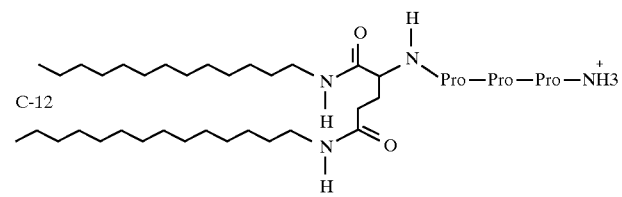

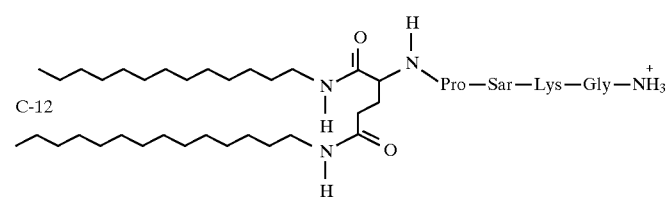

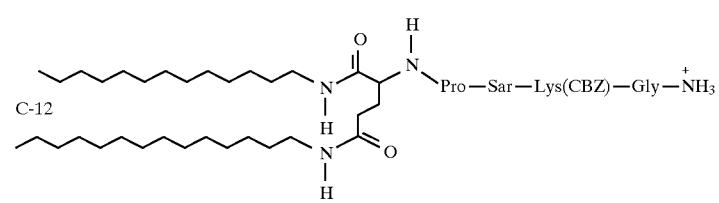

-continued
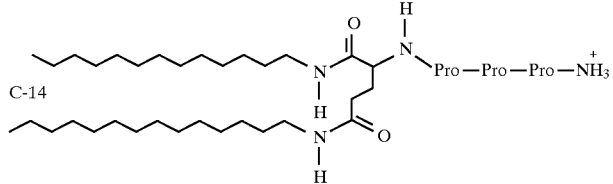
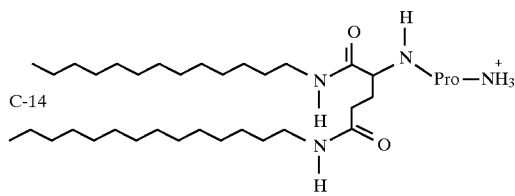
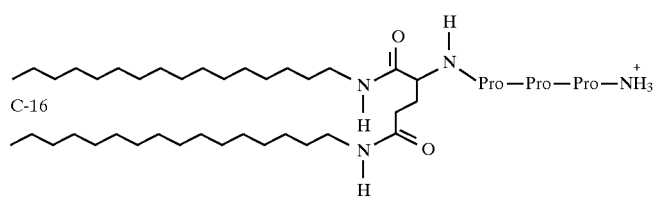
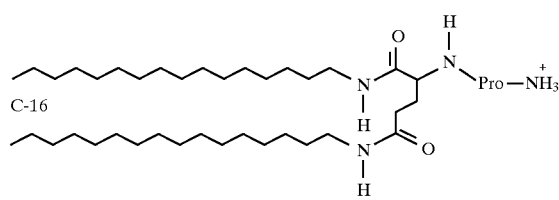
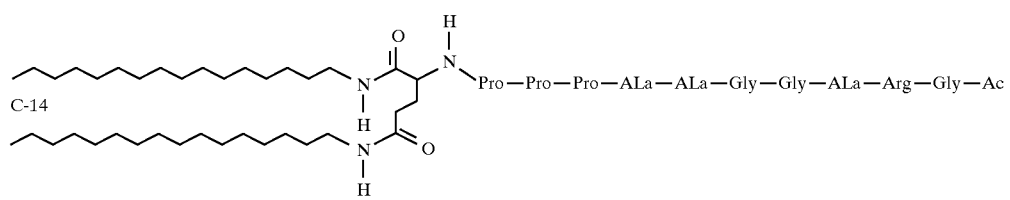
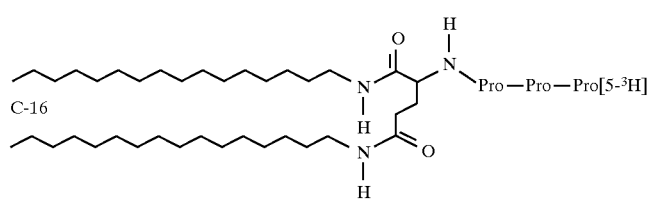
Compounds according to Formulas 5 and 6 also have been synthesized, and appear to form HAR microstructures when subjected to appropriate regimens.
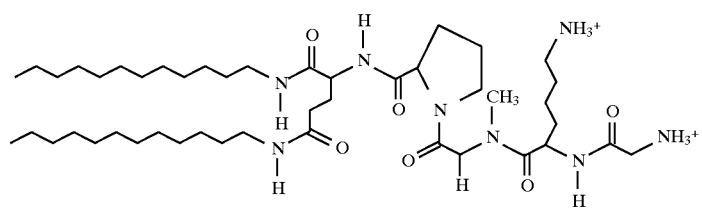
Formula 5

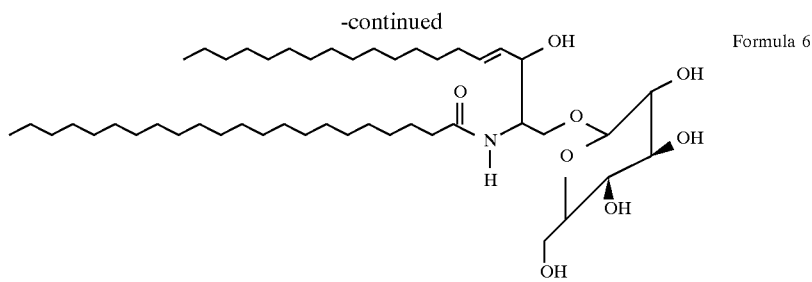

Formula 6

Several ceramide-type compounds also have been synthesized and are HARFMs. The ceramides comprise sphingosine acylated with fatty acids. Good results have been obtained using nervonic acid, or fatty acids similar thereto, coupled to sphingosine, or derivatives thereof, to provide N-nervonoyl ceramides. Nervonic acid was chosen for several reasons. First, it is present naturally in the body, and therefore should not be toxic. Second, it includes a site of unsaturation, i.e., a double bond, which currently is believed to favor formation of HAR microstructures relative to compounds which do not include sites of unsaturation. Various HARFMs also can be made by selectively coupling compounds to the 1° hydroxyl group provided by sphingosine. The compounds synthesized to date are shown below, and the synthesis of these compounds is further discussed in Example 5. The compounds shown below also can be acylated.

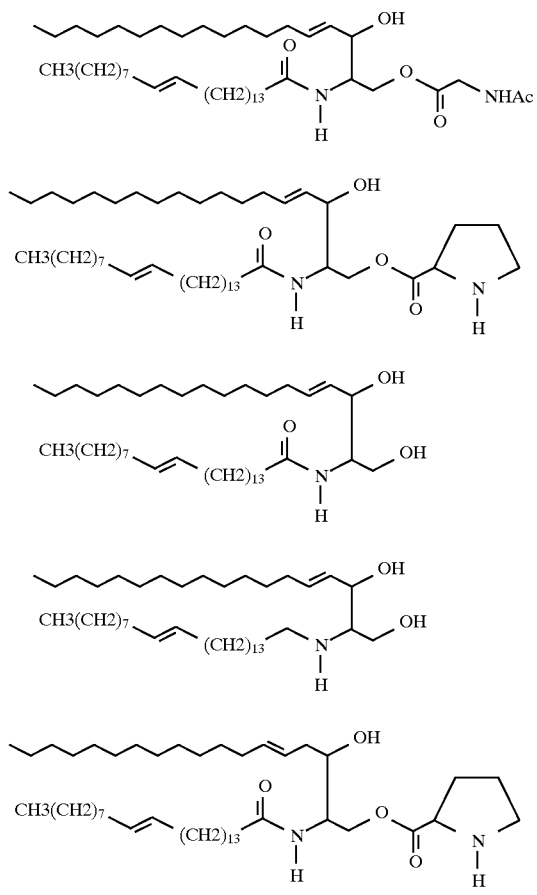

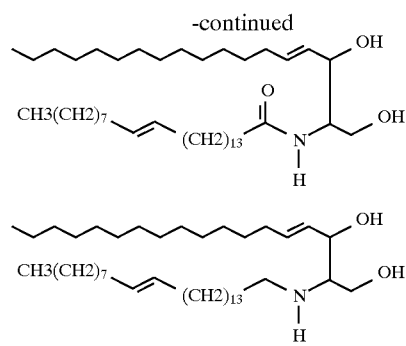

B. Therapeutics

Once an appropriate HARFM is selected and synthesized, a therapeutic compound also must be selected. The therapeutic compound (Th) is coupled, such as by covalent bonding, to individual HARFMs to form composite compounds. The therapeutic compounds can be conventional pharmaceuticals, peptides (such as oligopeptides, enzymes, etc.), nucleic acids (such as DNA and RNA), cells, antigens, etc. However, by way of example only, and without limitation, the following is a partial list of therapeutics that can be attached to HARFMs to form composite compounds.

1. Peptides

There are a number of peptides that currently are used for treating a variety of conditions and maladies. For instance, candidate peptides for attachment to HARFM include insulin, vasopressin, growth hormone, and any other natural or synthetic peptide ligand now known or hereafter discovered or synthesized for endogenous receptors. Peptides also can be used to form vaccines, such as orally administered vaccines. "Vaccine" generally refers to systems that deliver an antigen, generally a protein, in a controlled manner to elicit an immune response.

2. Steroids

Another example of a class of compounds commonly used as therapeutics are the steroids. Examples of candidate steroids for attachment to HARFMs include estrogen, progesterone and testosterone. Synthetic and/or semi-synthetic derivatives (eg estrone or methyl-testosterone) also can be used. Combinations of these steroids also may be used, such as are used in birth control formulations, and methylprednisolone, which is used as an anti-inflammatory corticosteroid.

3. Conventional Pharmaceuticals

Another class of candidate agents for attachment to CFMs are the conventional organic pharmaceuticals. Examples of such compounds, without limitation, include:

(1) antihypertensives, e.g., calcium channel blockers such as nifedipine and verapamil.

(2) vasodilators, such as nitroglycerin.

(3) diuretics, such as lasix and hydrochlorothiazide.

(4) psychotropics (benzodiazepines), such as diazepam.

(5) stimulants, such as methylphenidate.

(6) antidepressants, such as doxepin or serotonin specific re-uptake inhibitors including Prozac.

(7) antipsychotics, such as lithium and haloperidol.

(8) antiemetics, such as chlorpromazine or scopolamine.

(9) analgesics, such as acetaminophen and acetylsalicylic acid.

(10) non-steroidal anti-inflammatory drugs (NSAIDs), such as indomethacin or naproxen.

(11) histamine antagonists, such as cimetidine, ranitidine and diphenhydramine.

(12) narcotics, such as morphine and demerol.

C. Spacers

Figure 4:
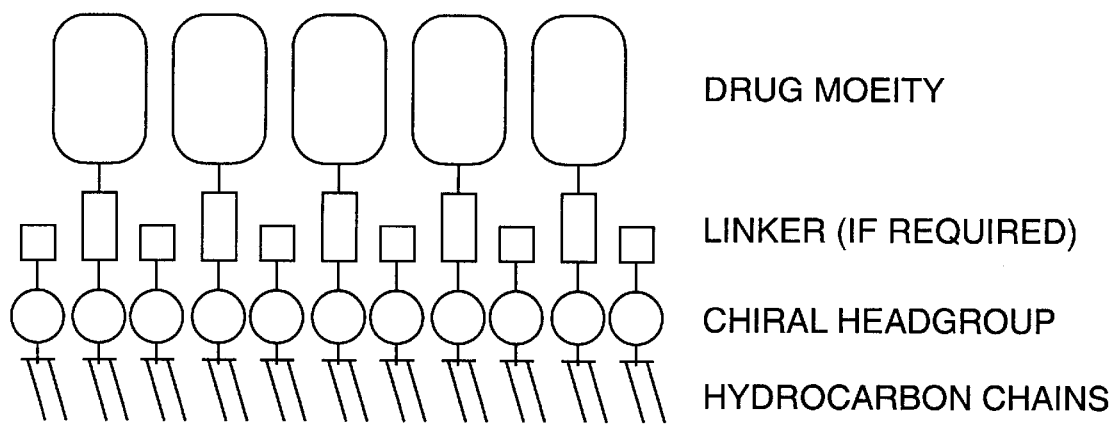
FIG. 4 is a schematic representation illustrating the use of spacers for coupling therapeutics to cylindrical microstructures.
Figure 5:
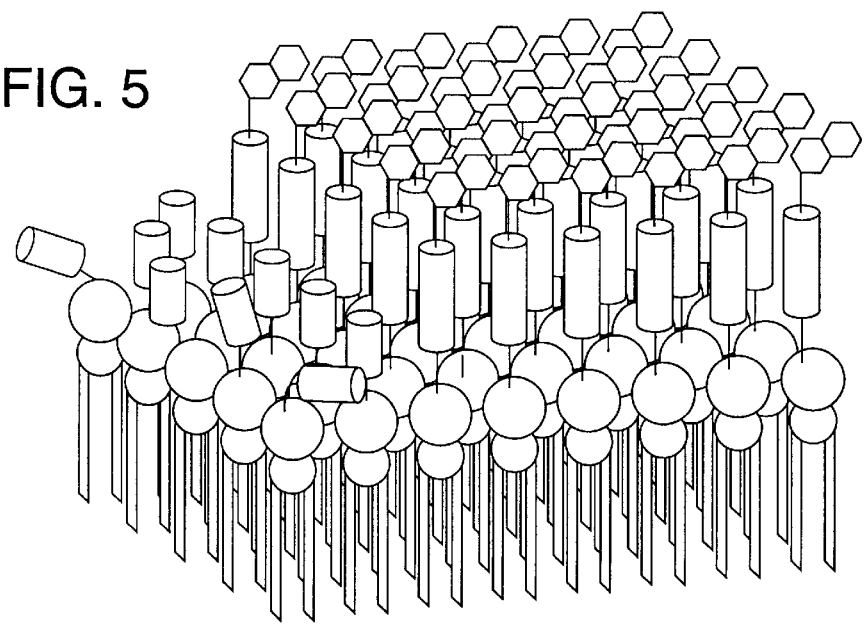
FIG. 5 is a schematic representation of a monolayer array of lipids at the edge of a tubule representing the enzymatic cleavage of a spacer.

The therapeutic compounds selected for coupling to the HARFMs can be directly coupled to the CFM. Alternatively, the therapeutic can be coupled to the HARFM using a spacer (spacers also are referred to as tethers and linkers), i.e., HARFM-S-Th. Spacers appear to uncouple the steric interactions of the agents from the packing of the HAR-forming lipids. The spacer might also provide a cleavage site recognized by an enzyme that is either dispensed in combination with the HARFMs-Ths compounds, or is endogenous to the environment in which the HARFMs-Ths are administered. See FIG. 4, which provides a schematic representation illustrating the use of spacers for coupling therapeutics to HAR microstructures.

Polypeptides are an example of a class of spacers useful for the present invention. Such polypeptides generally will include a sequence known to be susceptible to attack by a protease, such as, without limitation, trypsin and trypsin-like enzymes (trypsin cleaves on the carboxyl side of lysine and arginine residues) and elastase (which recognizes Ala-Ala-Ala sequences) at the site of use. For instance, compounds similar to that shown in Formula 6 have been made which include trypsin cleavage sites at different positions along the chain. Packing of the drugs at the surface of the microstructure generally is tight enough to prevent access by a protease. Only at the disordered ends of the HAR microstructures is there access to the cleavage site for enzyme activity. As a result, the release of the drug would be controlled by the constant number of intact spacers exposed at the advancing front.

Polypeptides are not the only compounds potentially useful as spacers for the purpose of separating the steric interaction between the HARFM and therapeutics. Alternatively, the spacer might include a functional group of limited stability against cleavage at the site of use. For example, the spacer might simply comprise alkyl, alkenyl or alkynyl carbon chains having a functionality that is readily cleaved in the environment in which the composite compounds are administered. Such compounds might be esters, as long as the ester functionality is sufficiently labile in the environment in which the composite compounds are administered to release Th upon hydrolysis. Alternatively, the spacers might comprise carbohydrates or polyoxyalkylenes, particularly polyoxymethylene and polyoxyethylene.

D. Forming Compounds Comprising HARFM-Th and HARFM-S-Th

The following paragraphs discuss attaching particular classes of compounds to HARFMs to form the composite HARFM-Th or HARFM-S-Th. Specific guidance as to the means for attaching Th to a particular HARFM depends upon several factors, including the nature of the HARFM, the Th, and on the environment in which the composite compounds will be administered. However, in general the head group of the HARFMs include nucleophilic groups, such as amine and hydroxyl groups. These nucleophilic groups can be reacted with electrophilic species to couple the agents to the HARFMs.

1. Peptides

Peptides, such as insulin and enkephalins, are an important class of compounds that can be delivered using HARFMs. Peptides of any desired sequence can be synthesized using standard synthetic techniques, such as solid-phase synthesis using Applied Biosystems Peptide Synthesizers or other available devices. In order to couple the peptide to the a-amino group of dialkylated glutamine compounds or glutamic acid lipids, the peptide is prepared with its N-terminus and all of its reactive side chains in protected form. Moreover, the peptide includes a free C-terminal carboxyl group. This is accomplished using a special peptide synthesis resin called super acid-sensitive resin, known as SASRIN, which is available from Bachem, Inc. The fully protected peptide is cleaved from the resin with mild acid, such as 1% trifluoroacetic acid in methylene chloride. This leaves the side chain and N-terminus protecting groups intact.

Peptide synthesis is accomplished with the α-amino groups of the amino acids protected, such as with a fluorenylmethyloxycarbonyl (FMOC) protecting group, and bearing standard side-chain protecting groups that are removed with strong acid (i.e., trityl, t-butyl, etc.). After the N-terminal amino acid is attached to the polypeptide, the FMOC group can be left on and removed along with the side chain protecting groups after the peptide is coupled to the lipid. Alternatively, the FMOC protecting group can be removed while the peptide is still bound to the resin. This allows modifications of the N-terminus, such as by modifying the N-terminus with probes. Probes containing an N-hydroxylsuccinimide ester or an isothiocyanate can be used for attachment to the peptide N-terminus.

After the polypeptide is cleaved from the SASRIN resin, it is then coupled to the a-amino group of dialkylated glutamine compounds or glutamic acid lipids using either dicyclohexylcarbodiimide or diethyl phosphorylcyanate in a solvent such as DMF or methylene chloride. The coupling is monitored by observing the loss of the lipid $NH_2$ group using the Kaiser test. Kaiser et al.'s *Color Test for Detection of Free Terminal Amino Groups in the Solid-Phase Synthesis of Peptides*, 34:595–598 (Anal. Biochem., 1970). After coupling, the crude material is treated with neat trifluoroacetic acid containing the appropriate scavengers (thioanisole, 1,2-dithioethane, etc., depending on the structure of the side-chain protecting groups). The crude lipidic-peptides are purified by HPLC on a reverse-phase column.

2. Nucleic Acids

Nucleic acids useful in the practice of the present invention comprise isolated nucleic acids. An "isolated" nucleic acid has been substantially separated or purified away from other nucleic acid sequences in the cell of the organism from which it naturally occurs, i.e., other chromosomal and extrachromosomal DNA and RNA. The term thus encompasses nucleic acids purified by standard nucleic acid purification means. It also embraces nucleic acids prepared by recombinant expression in a host cell and chemically synthesized nucleic acids. Also included are nucleic acids that are substantially similar to such nucleic acids. Methods for chemical synthesis of nucleic acids are discussed, for example, in Beaucage and Carruthers, Tetra. Letts. 22:1859–1862, 1981, and Matteucci et al., J. Am. Chem. Soc. 103:3185, 1981. Chemical synthesis of nucleic acids may be performed, for example, on commercial automated oligonucleotide synthesizers.

Desired nucleic acid compounds can be attached to the HARFMs by a variety of methods. However, by way of example only and without limitation, nucleic acids can be coupled to HARFMs using the 5'-hydroxyl group. This hydroxyl group can be used to link nucleic acids to the HAR-forming lipids via an ester functionality. Because a number of the HAR-forming lipids used for the present invention have amines at the head group (See, for instance, the compounds of Table 1), an additional group containing a free carboxyl group must be used to couple the nucleic acids to the HAR-forming lipids. For example, peptide spacers comprising amino acids having a side-chain carboxyl group could be used to couple nucleic acids to the HARFMs. Aspartic and glutamic acid are examples of amino acids having a carboxyl functionality that could be included in the peptide spacer to link nucleic acids to the HARFM-forming molecules.

3. Conventional Pharmaceuticals

Conventional pharmaceuticals also can be attached to the HARFMs. The method for attachment depends on the particular HARFM and therapeutic selected. However, solely by way of example, the following provides a discussion concerning the attachment of particular classes of conventional therapeutics to HARFMs.

a. Steroids

Steroids generally have a hydroxyl group in the A ring (the first 6-membered ring). This hydroxyl group can be used to link steroids to the HAR-forming lipids via an ester functionality as discussed above for nucleic acids. Because a number of the HAR-forming lipids used for the present invention have amines at the head group (See, for instance, the compounds of Table 1), an additional group containing a free carboxyl group must be used to couple the steroid to the HAR-forming lipids. Amino acids having a carboxyl group in a side chain could be included in peptide spacers to link steroids to the HAR-forming molecules.

b. Acetylsalicylic Acid

Acetylsalicylic acid (aspirin) is an additional example of a conventional therapeutic that could be delivered using HAR-forming lipids. Acetyl-salicylic acid includes a carboxyl group that could be used to form an amide with an amine or an ester with a hydroxyl group. As stated above, a number of the HAR-forming lipids have amines at the head group of the lipid. The amine could be used to form an amide with the carboxyl group of acetylsalicylic acid.

HAR-forming lipids that include hydroxyl groups could be directly attached to acetylsalicylic acid via an ester. HAR-forming lipids that have amines at the head group generally will be coupled to compounds such as acetylsalicylic acid using spacers. For example, polypeptide spacers could be used for this purpose wherein at least one of the amino acids in the polypeptide includes a side chain having an hydroxyl group, such as serine. The side-chain hydroxyl group could be coupled to the carboxyl group of acetylsalicylic acid via an ester functionality.

II. HAR-FORMING REGIMENS AND MICROSTRUCTURE MORPHOLOGY

Once the HARFMs and Ths are coupled, the composite compounds, or just the HARFMs, are then subjected to HAR-forming regimens. The conditions required to form the desired microstructures may differ from compound to compound, although all the surfactants synthesized form aggregates in water because of their hydrophobic tails. The following procedures have proved most useful for inducing the HAR microstructures in the compounds tested to date.

(1) heating a suspension of lipids in water to a temperature above $T_m$ (lipid hydrocarbon chain melting temperature), followed by slow cooling through $T_m$;

(2) heating a suspension of lipids in water to a temperature above the $T_m$, sonicating to form small unilamellar vesicles (SUVs), cooling to a temperature well below $T_m$ until extended multilamellar sheets are formed, heating slowly to above $T_m$ and then cooling slowly to a temperature below $T_m$;

(3) at $T<T_m$, completely dissolving lipid in a water-miscible solvent, such as an alcohol, and adding an appropriate ratio of a non-solvent, such as water, until HAR microstructures precipitate directly from the mixture (Georger et al.);

(4) at $T>T_m$, completely dissolving lipids in a water-miscible solvent, adding a nonsolvent such as water and lowering the temperature slowly to below $T_m$ (Jerome Lando et al.);

(5) suspend lipid at $T<T_m$ in a water/glycol mixture, heating to $T>T_m$, cool to a $T<<T_m$ and repeating at least one more time (this method was developed by Archibald and Yager for forming tubules from NFA-cer and cochleates from HFA-cer);

(6) dispersing and/or sonicating lipids above $T_m$, and cooling to below $T_m$ and waiting for the microstructures to form (this method is generally applicable to materials having a high CMC);

(7) precipitation upon dilution of concentrated methanol solution of peptide lipids with aqueous media;

(8) thermal cycling, plural times, peptide lipid suspensions in pure aqueous buffer;

(9) thermal cycling, plural times, of peptide lipid suspensions in mixtures of aqueous buffers and alcohols; and

(10) dissolving lipids in a solution of a detergent, such as TRITON X-100, at a concentration greater than the CMC of the detergent, followed by dialysis of the mixture to remove the detergent.

Each of these methods also may involve varying certain steps to maximize the formation of cylindrical microstructures. For instance, the pH may have to be adjusted to account for different association tendencies for particular compounds.

Certain tubule- and cochleate-forming techniques also are described in detail in the following references, each of which is incorporated herein by reference. Yager et al.'s *Formation of Tubules by a Polymerizable Surfactant*, 106:371–381 (Mol.Cryst. Liq. Cryst., 1984); Yager et al.'s *Two Mechanisms for Forming Novel Tubular Microstructures from Polymerizable Lipids*, 49:320 (Biophys. J., 1986); Yager et al.'s *Helical and Tubular Microstructures Formed by Polymerizable Phosphatidylcholines*, 109:6169–6175 (J. Am. Chem. Soc., 1987); Yager et al.'s *Microstructural Polymorphism in Bovine Brain Galactocerebrosides and its Two Major Subfractions*, 31:9045–9055 (Biochemistry, 1992); Yager et al.'s *A Model for Crystalline Order Within Helical and Tubular Structures of Chiral Bilayers*, 58:253–258 (Chemistry and Physics of Lipids, 1991); Yager et al.'s U.S. Pat. No. 4,911,981, entitled *Process for Fabrication of Lipid Microstructures*; Yager et al.'s U.S. Pat. No. 4,990,291, entitled *Method of Making Lipid Tubules by a Cooling Process*; and Yager et al.'s *Method of Making Lipid Tubules by a Cooling Process*, D.o.t.N.G., Inc., Editor (1991).

The microstructures formed in accordance with the general procedures outlined above, and as described in more detail in the examples, can be confirmed using a light microscope for lipid microstructures having dimensions larger than about 1 $\mu$m. A Zeiss ICM-405 inverted microscope has been equipped for epifluorescence illumination, brightfield, and phase contrast imaging; attachments include a 63×1.40 NA Planapochromat, a 35 mm camera, and a Peltier effect microscope stage for sample temperature control (−20° to +100° C., +/−0.1° C.). A Dage 66 SIT video camera (with S-VHS VCR and monitor) allows video imaging through the microscope in all imaging modes. Image processing and printing from live or stored video is possible using a Data Translation QuickCapture frame grabber board in a Macintosh II. This system allows imaging of HAR microstructures at video rates.

Certain microstructures are too small to be visualized using an optical microscope. For imaging microstructures too narrow to be resolved by optical microscopy, such as those expected from some of the surfactants with polypeptide headgroups, transmission electron microscopy (TEM) can be used, such as the TEM of the University of Washington's Medical School Imaging Center. Imaging can be either direct or with a phosphotungstic acid negative stain. Freeze fracture replicas can be made using a Balzers 360 belonging to the Imaging Center. Additional techniques can be used to characterize the compounds formed, including circular dichroism (CD) and Raman spectroscopy.

Examples 6–13 below illustrate certain methods for forming HAR microstructures, and the morphologies of the structures made.

III. STABILITY OF HARFMs AT PHYSIOLOGICAL CONDITIONS

The stability of the compounds made in accordance with the present invention also has been investigated. HARFMs formed as described above were subjected to tests to determine the thermal stability of the compounds at physiological temperatures and physiological pH. Examples 14–15 provide more detail concerning how thermal and physiological-fluid tests were conducted. In general, HAR therapeutics formed in accordance with the present invention were stable at physiological pH and physiological temperatures, particularly those materials having $T_{Ms}$ greater than physiolgoical temperature.

IV. KINETICS OF DISSOLUTION AND ENZYMATIC CLEAVAGE

There at least two mechanisms for dissolution and enzymatic cleavage of HAR therapeutic agents made in accordance with the present invention. In the first scenario, the HARFM comprises an HAR-forming surfactant with a therapeutic covalently attached to its headgroup. The surfactant would be a lipidated drug if it were active in its intact form. However, if the therapeutic is released or activated by cleavage, such as enzymatic cleavage, after entering the target cell, then the compounds of the present invention function as lipidated prodrugs. The constant rate of cylinder dissolution appears to be controlled largely by the solubility of the lipidated drug in the surrounding medium. The greater the ratio of head-group area to hydrocarbon chain surface area, the more rapid will be the dissolution and delivery.

In the second approach, the drug moiety is attached to the HAR-forming surfactant via a cleavable spacer (sometimes referred to as a tether) as discussed in more detail below. In general, spacers might be a polypeptide with a sequence known to be susceptible to attack by a protease at the site of use, or a functional group of limited stability against cleavage when exposed to the solution at the site of use. The drugs are packed tightly enough at the surface of the HARFM microstructure to prevent access by a protease. Only at the disordered ends of the HARFMs would there be access for the enzyme to interact with the HAR microstructures so that the release of the drug would be controlled by the constant number of intact spacers exposed at the advancing front of spacer cleavage. While this approach seems more complex, it allows using a single HARFM and spacer for coupling to a wide range of water-soluble molecules, including biomolecules such as polypeptides and nucleic acids.

HARFMs, particularly tubules and cochleate structures, generally are crystalline materials and tend to dissolve only from the surfaces and ends thereof, or perhaps from regions of imperfection in the HAR microstructure. The end-dominated dissolution model and lysis was evaluated both theoretically and empirically.

A. Theoretical Evaluation

Theoretical dissolution rates of three structures—a solid sphere, an infinitely long solid cylinder, and a slab were used to model the kinetics for dissolution at HAR microstructures, particularly tubule and cochleate ends. In all cases the dissolution rate is proportional to the exposed surface area. The three are drastically different when considering one particle or a homogeneous population of particles. However, heterogeneity in particle size softens the distinction between the models.

Figure 6:
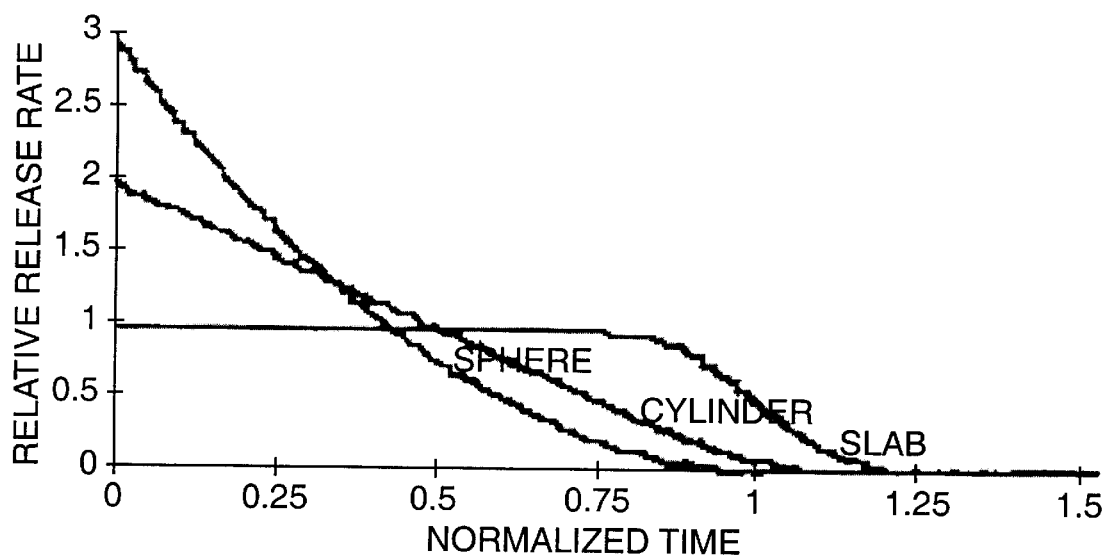
FIG. 6 is a graph that compares the kinetics of dissolution of spheres, infinitely long solid cylinders (no diffusion from the ends) and flat slabs (for modeling dissolution from the ends of tubules).
Figure 7:
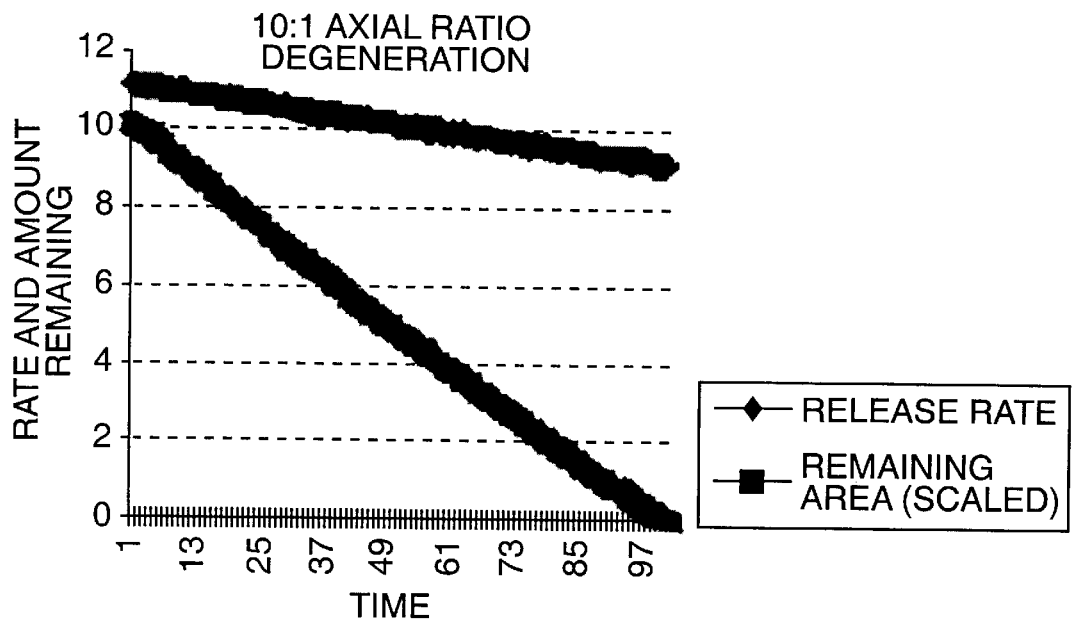
FIG. 7 is a graph illustrating the calculated degradation of a flat sheet having a 10:1 axial ratio that is degrading from its edges at a rate proportional to the length of its edges as a model of the degradation of cochleate cylinders.

As shown in FIG. 6, the nature of the dissolution can be distinguished by the number and position of inflection points in the delivery rate curve. FIG. 6 shows that the relative release rate depends upon the morphology of the system. Both the sphere and the infinitely long solid cylinder exhibited dissolution rates that varied from relative rates of 2 or greater to 0 over the time period tested. On the other hand, the solid slab, which was used to model dissolution from tubules and cochleate structures, had a relative dissolution rate of about 1 over virtually the entire period tested.

The rate of appearance of dissolved surfactant or surfactant breakdown products from tubules appears to remain substantially constant until the number of tubules (and ends) declines. The rate of drug release to the tissue is limited by the rate of release from the ends of tubules, so that drug release rate generally is constant (0-order), as opposed to the more conventional first-order kinetics found with a wide range of other geometries.

Cochleate cylinders consist of one or more bilayers that have wrapped in a helical manner to form the cochleate microstructure. Cochleate cylinders therefore have two types of "free edges"; those at the microstructure ends, and one or two bilayer edges along the length of the microstructure. As a result, an appropriate model for the dissolution or enzymatic degradation of cochleate cylinders is the unrolled flat sheet that comprises the microstructure. In this model, very long and very short cochleate cylinders both can degrade with kinetics similar to those of the lipid tubules. If the sheet that wraps to form the cochleate cylinder has an axial ratio of about 10:1, there is only an 18% decrease in the hydrolysis or degradation rate before the microstructure is completely hydrolyzed or degraded (if the ratio is greater than 10:1, then the decrease in the hydrolysis rate or degradation rate is concomitantly decreased). As stated above, the cochleate cylinder formed by wrapping such a sheet has an axial ratio of greater than 300 (30 µm in length divided by 0.1 µm in diameter=300). However, if the sheet is nearly square then the rate of hydrolysis or degradation will decrease linearly until the cochleate microstructure is completely hydrolyzed or degraded.

The rate of drug release generally will only be constant to the extent that the HAR microstructure population is homogeneous in length. While is it possible to form HAR microstructures with unimodal length distributions using particular crystallization methods [See, for instance, the crystallization protocol discussed in Yager et al.'s *Helical and Tubular Microstructures Formed by Polymerizable Phosphatidylcholines*, 109:6169–6175 (J. Am. Chem. Soc., 1987)] there is always a distribution of lengths about the mean. Storing the HAR microstructures often results in the smaller HAR microstructures converting to longer ones. It is possible to remove the extremes of the length distribution using filtration and sedimentation.

B. Empirical Studies

1. Proof-of-Principle Experiment

A proof-of-principle experiment was performed on $DC_{8,9}PC$ which is commercially available (Avanti Polar Lipids, Birmingham Ala.). The experiment was performed to prove that tubules could be enzymatically cleaved (and release fatty acid) at a constant rate. The enzyme phospholipase $A_2$ ($PLA_2$) is known to hydrolyze the fatty acid at the 2 position of the glycerol backbone of phospholipids. It is also known that $PLA_2$ only binds tightly to bilayers in the presence of negatively charged lipids such as fatty acids; once some hydrolysis has occurred, the proportion of membrane-bound enzyme increases. $PLA_2$ is known to hydrolyze the well-studied dipalmitoyl phosphatidylcholine (DPPC) below its Tm. An experiment was designed to determine whether $PLA_2$ can work on $DC_{8,9}PC$ below its $T_M$ in tubule form.

Figure 8:
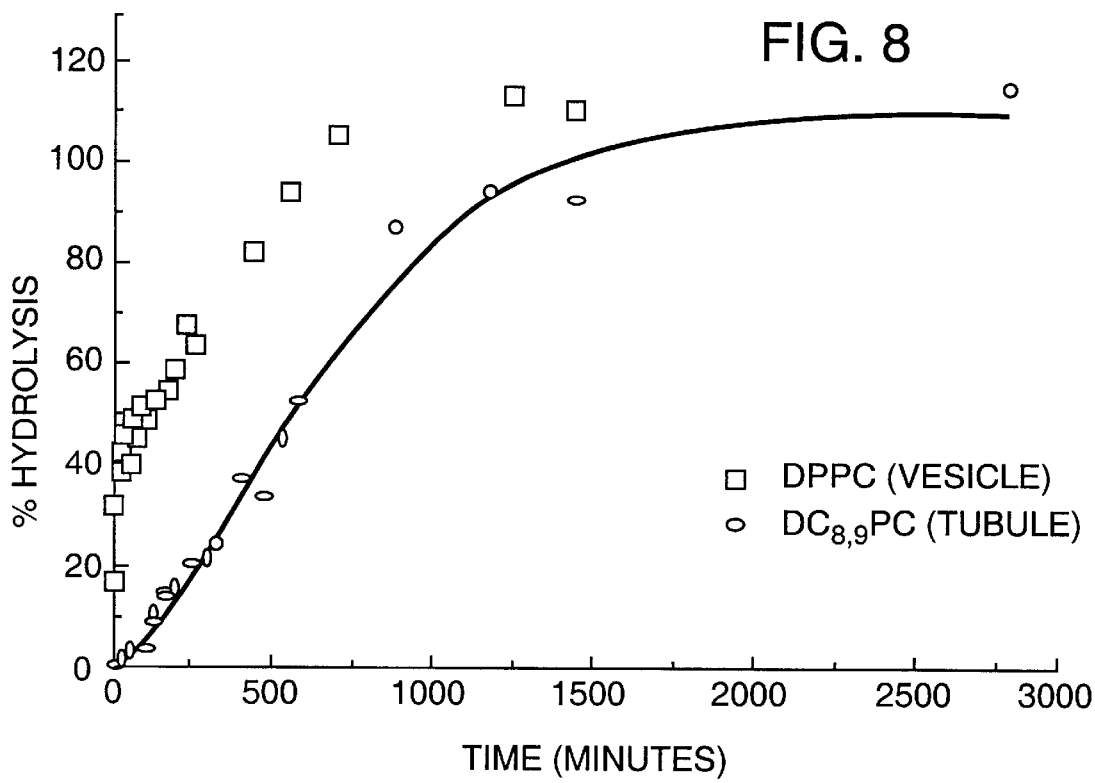
FIG. 8 is a graph of time versus % hydrolysis for suspensions of $DC_{8,9}PC$ tubules and DPPC liposomes by 160 nM cobra venom $PLA_2$.

Small unilamellar vesicles (SUVs) were prepared from 1,2-dipalmitoyl-sn-glycero-3-phosphocholine (DPPC). The $T_M$ of DPPC at 41.3° C. is similar to that of $DC_{8,9}PC$, and is only slightly depressed in SUVs. Because they have identical head groups, comparison of hydrolysis of DPPC vesicles and $DC_{8,9}PC$ tubules allows isolation of those effects unique to a tubular microstructure. FIG. 8 shows the progress curves for the hydrolysis of 0.5 mM dispersion of DPPC SUVs and of multi lamellar $DC_{8,9}PC$ tubules at 30° C. by 2.24 μg/ml $PLA_2$ as determined by the production of free fatty acid. The hydrolysis progress curve for the control SUV dispersion of DPPC was biphasic, as expected. An initial rapid hydrolysis stage, which ends after roughly 50% of the total lipid has been hydrolyzed, is followed by a period of slower, nearly constant hydrolysis. In a unilamellar liposome, only the outermost layer is initially accessible to enzyme. The rapid initial hydrolysis rate of 0.88 $s^{-1}$ reflects the hydrolysis of lipids in the outer monolayer. The onset of the subsequent slower hydrolysis stage is caused by substrate depletion in the outer monolayer. Hydrolysis proceeds to completion at about 0.044 $s^{-1}$, limited by access to new substrate either from the bursting of partially hydrolyzed vesicles or from slow phospholipid flip-flop between the inner and outer vesicle monolayers.

The progress of tubule hydrolysis is markedly different. After a 120 minute lag, the hydrolysis proceeds with a slow, nearly constant rate of 0.041 $s^{-1}$ for most of the reaction. The rate of hydrolysis of tubules after the initial lag is 20 times slower that for the outermost DPPC vesicle monolayer, and, in contrast to all other reported $PLA_2$ reaction profiles, it remains constant after the initial lag until nearly 100% hydrolysis. This constant hydrolysis rate is consistent with end-dominated tubule hydrolysis.

However, the microstructures observed by TEM reflect a more complex process. Shortly after addition of enzyme, helical ribbons emerging from what appear to be fractured tubules are visible. Even though a few intact tubules are still present at the 50% hydrolysis point, the types of microstructures present include small filaments, helical ribbons, and elongated sheets. Tubules appear to remain intact until certain fraction of reaction products is reached within a local region of the tubule bilayer. The point when product accumulation can no longer support the specific asymmetric curvature required to form a one micrometer diameter tubule, the product regions fracture and unwrap to form smaller helices, filaments and flat sheets.

Moreover, fluorescent dye studies have been completed, wherein the cationic fluorescent dye 1,1,3,3,3',3'-hexamethyl-indocarbocyanine iodide was added to visualize the region of negative charge accumulation. Early in the reaction, fluorescent regions appear at several point along intact tubules. Hydrolysis, therefore is not limited to tubule ends. Instead, local defects in molecular packing within the bilayer appear to function as initiation sites for hydrolysis.

Fluorescent $PLA_2$ also has been used to track reaction progress. 5-carboxyfluorescein-tagged $PLA_2$ was used. Immediately after addition, enzyme appears to distribute uniformly over the tubule surface. By the completion of hydrolysis, the product microstructures show strong fluorescence, which implies enhanced $PLA_2$ binding to product-risk microstructures.

Although enzyme reaction with tubules is not limited to reaction at the end of tubules, the reaction progress nevertheless is still more constant and slower than that of SUVs. This makes the tubules attractive drug delivery agents.

2. Deterrent Dissolution Kinetics

Bile salts occuring naturally in humans act similarly to detergents. Thus, the kinetics of HAR microstructure dissolution in detergents is a good model for the oral administration of therapeutics and vaccines for delivery to the gastrointestinal tract. The kinetics of dissolution in detergent solutions has been investigated. The commercially-available tubule-forming phospholipid 1,2-bis(10,12-tricosadiynoyl)-sn-glycero-3phosphocholine ($DC_{8,9}PC$) and the non-ionic detergent octyl β-D-glucoside (OG) were used as the model system. Upon precipitation from ethanol, $DC_{8,9}PC$ forms multi-lamellar tubules with an average diameter of 0.75 μm, a length distribution ranging from 30–50 μm, and a melting temperature ($T_m$) of 43.8° C. The tubule morphology is composed of helically-wrapped lipid bilayers that close to form straight, hollow, rigid tubes. Tubules can appear, however, in the presence of minority structures such as open helical ribbons. If given time to anneal, the lipids form closed and uniform tubules. Presumably, the tight crystalline packing of the tubule wall will hinder release of monomeric lipid from the microstructure and insertion of detergent into the tubule except at regions of defects in the crystalline packing such as must occur at tubule ends or at "helical" defects.

Figure 9:
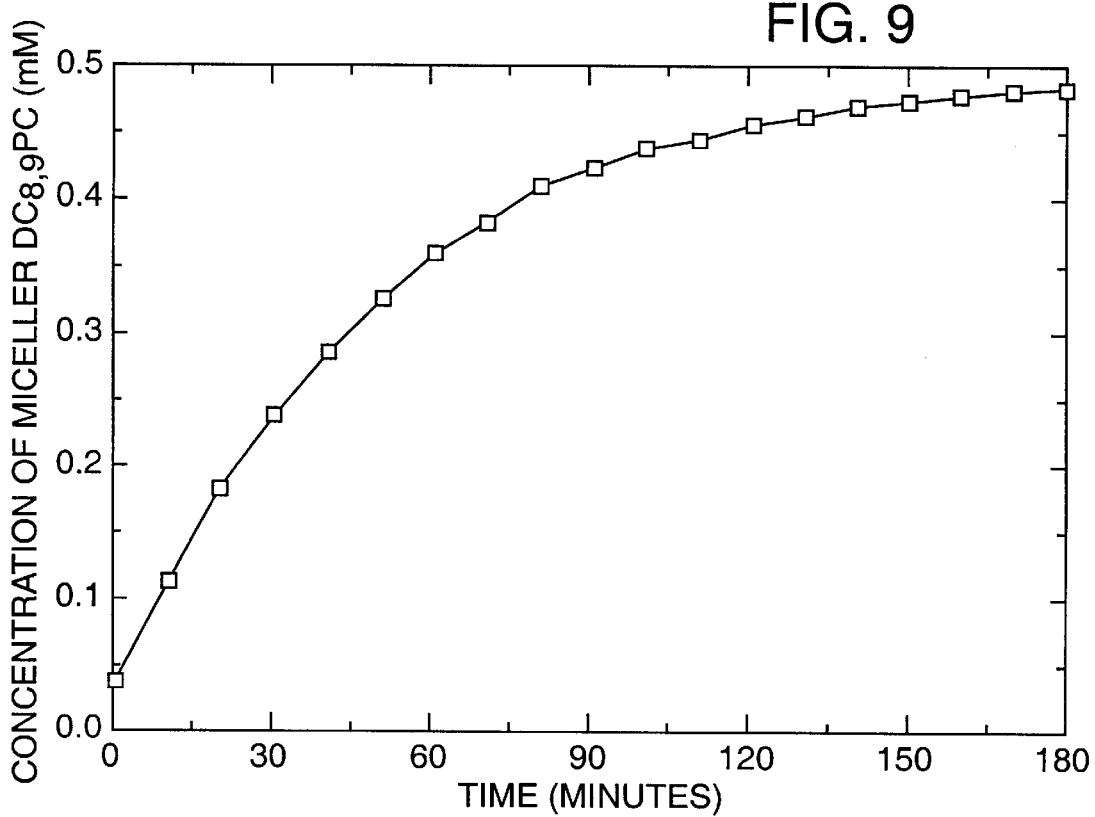
FIG. 9 is a graph of time versus concentration of micellar $DC_{8,9}PC$ illustrating the time course for the solubilization of a 0.5 mM suspension of $DC_{8,9}PC$ lipid tubules in the presence of 50 mM OG.
Figure 10:
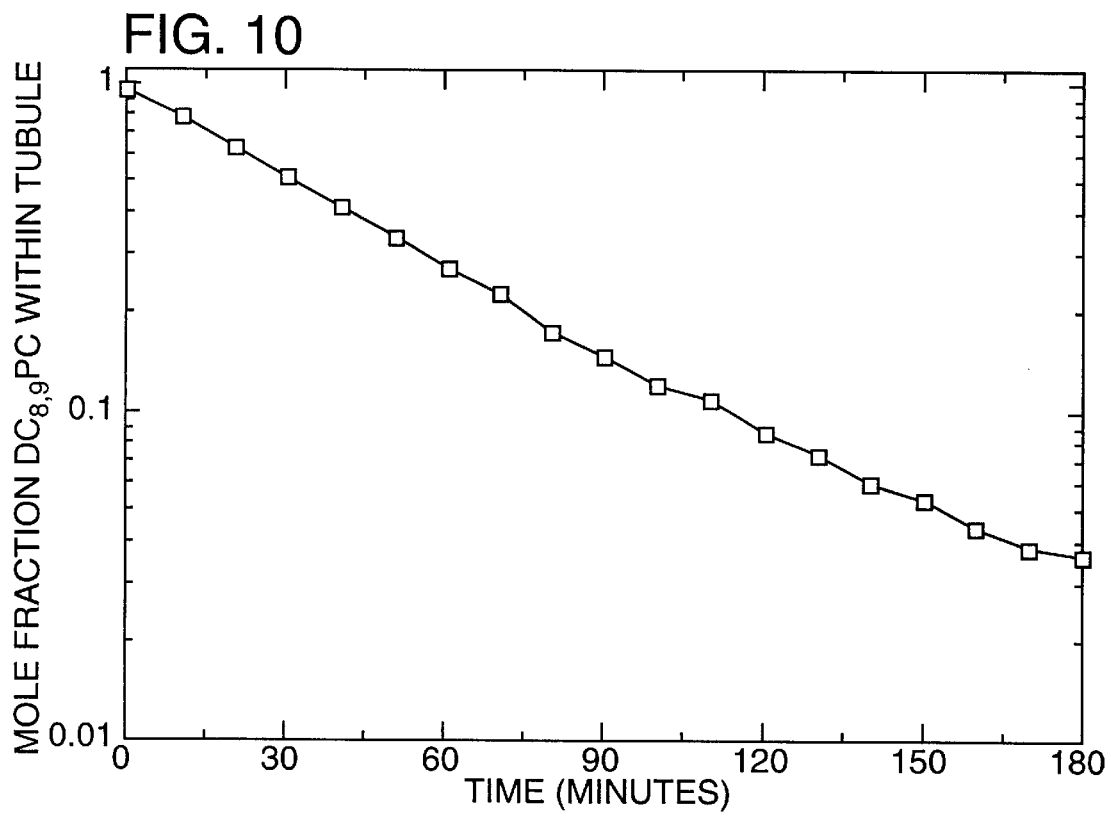
FIG. 10 is a graph of time versus the mole fraction of $DC_{8,9}PC$ remaining in tubule microstructures as a function of time.

FIG. 9 shows the concentration of $DC_{8,9}PC$ solubilized into OG detergent micelles as a function of time. To start solubilization, an aqueous suspension of $DC_{8,9}PC$ tubules was added to an aqueous suspension of OG detergent micelles to create a final solution having a 0.5 mM concentration of $DC_{8,9}PC$ and a 50 mM concentration of OG. The reaction vessel was at room temperature (approx. 21° C.). Tubule microstructures were much larger than detergent micelles so a 0.2 μm filter was used to separate the two phases prior to analysis. $DC_{8,9}PC$ absorbs strongly from 190 to 254 nm because of the diacetylene groups present in the hydrocarbon tails. The amount of micellar $DC_{8,9}PC$ was determined with a UV-Vis spectrometer by calculating the second derivative of the optical density with respect to wavelength at 250 nm, which was a mathematical step that reduced errors introduced from scattering artifacts. The concentration could be determined by comparing this value to those obtained from a calibration curve. Throughout the course of solubilization, aliquots of the suspension were removed, passed through a 0.2 μm filter, and assayed for the amount of solubilized $DC_{8,9}PC$. FIG. 10 shows the mole fraction of $DC_{8,9}PC$ remaining within a tubule as a function of time and depicts the nature of the solubilization process. The logarithm of the $DC_{8,9}PC$ tubule concentration depends linearly with time, which suggests that tubule disintegration is a first order process. Furthermore, changes in solution turbidity, as determined by measuring the optical density at 400 nm, correlates well (e.g. linearly) with the amount of $DC_{8,9}PC$ within the tubule.

Figure 11:
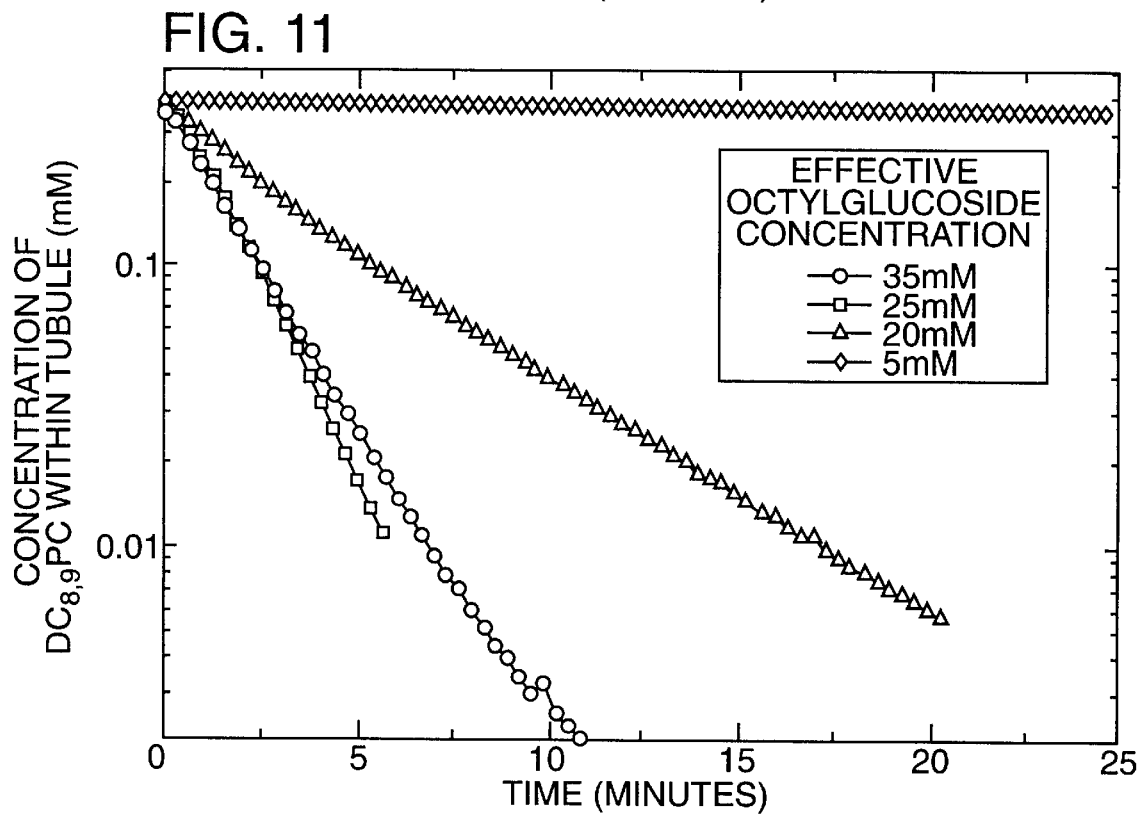
FIG. 11 is a graph of time versus concentration of $DC_{8,9}PC$ within tubules (mM) for various concentrations of solubilizing detergent.

Multilamellar PC tubules, L, interact with detergent, OG, to form mixed micelles, M. If, however, the effective concentration of detergent that is available for solubilization does not change throughout the course of the reaction (e.g. detergent is not consumed by the reaction, mixed micelles can contain many phospholipids, etc.), then the kinetics can be described as a first order process. If this view is correct, then the effective rate constant, $k_1$, should depend linearly on the concentration of detergent (e.g. $k_1=k_2$ [OG]). FIG. 11 shows the time course of solubilization as a function of OG concentration. An estimate for the value for the second order rate constant, $k_2$, can be determined from the slope of the line created when the measured first-order rate constant $k_1$, is plotted against detergent concentration.

$$k_2 = 0.124 \pm 0.012 \, mol_{-1}s^{-1}$$

Figure 12:
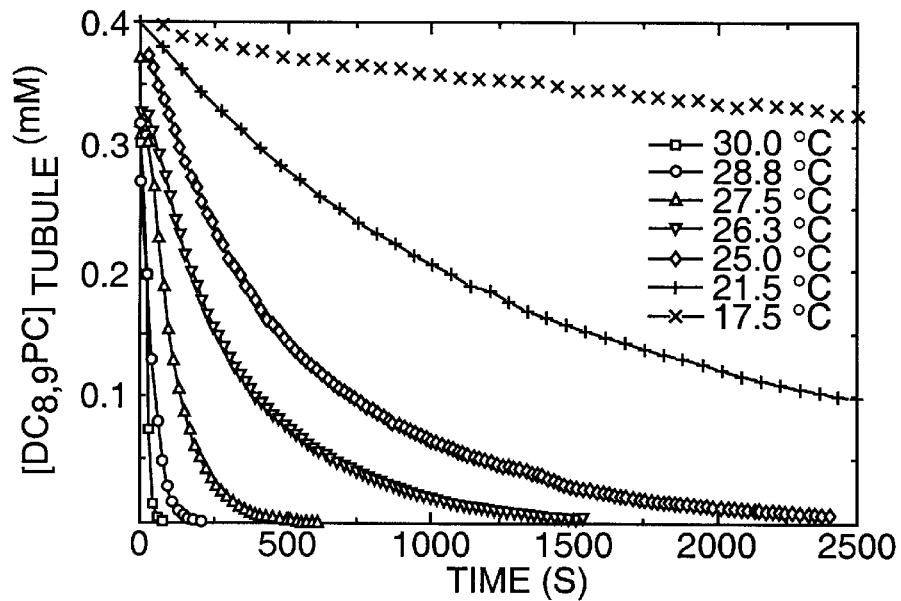
FIG. 12 is a graph of time versus concentration of $DC_{8,9}PC$ within tubules (mM) illustrating the temperature dependence on the concentration of $DC_{,8,9}PC$ within tubule microstructures.
Figure 13:
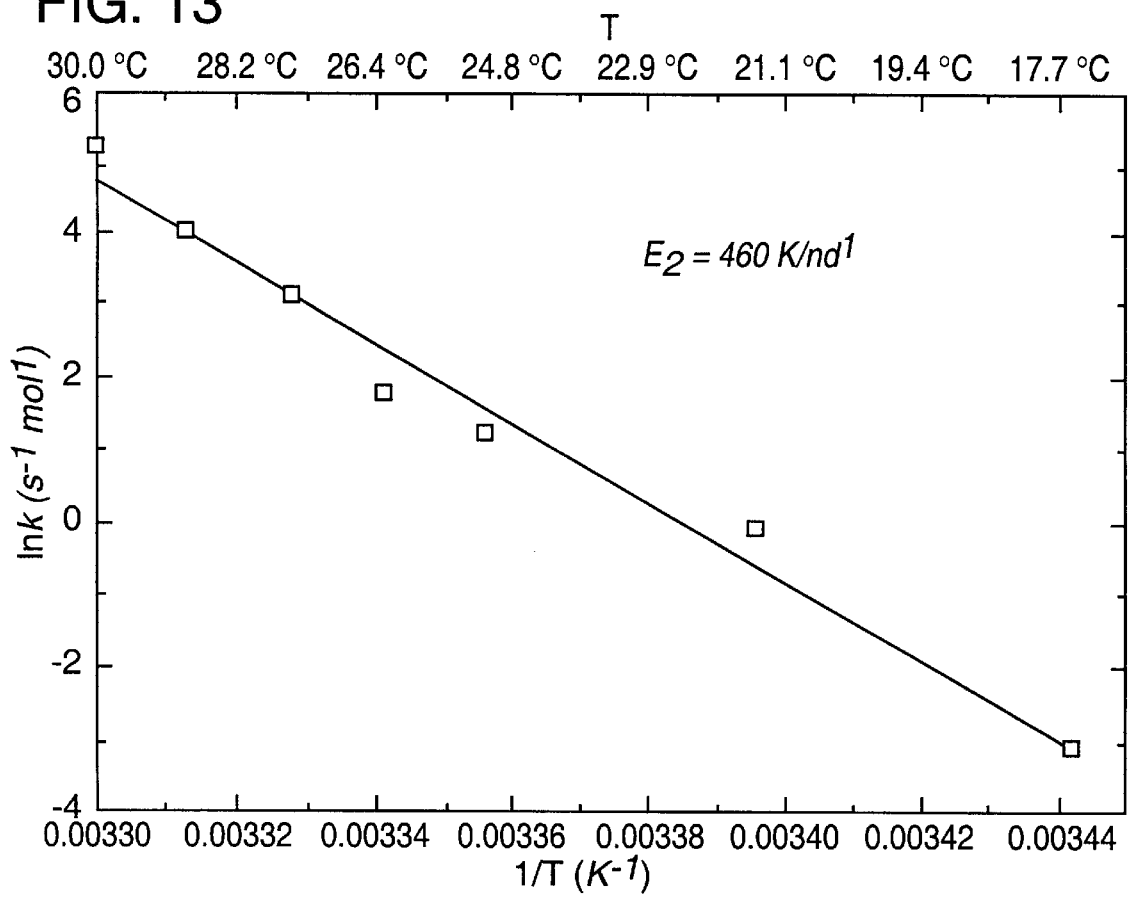
FIG. 13 is an Ahhrenius plot of the solubiliztion rate versus inverse temperature.

Temperature strongly affects the rate of HAR solubilization. FIG. 12 shows the concentration of $DC_{8,9}PC$ within a tubule as a function of time as determined from measuring the O.D. at 400 nm. A solution containing a 100-fold molar excess of OG (40 mM) was added to a stirred quartz cuvette and placed in a temperature-controlled UV-Vis spectrometer. Once the detergent suspension had reached thermal equilibrium, an aqueous suspension of $DC_{,8,9}PC$ tubules (0.4 mM) was quickly added. The temperature dependence of the rate of tubule solubilization was determined by measuring the decrease in turbidity (e.g. changes in O.D.) with time. As shown in FIG. 15, the kinetics of solubilization were strongly temperature dependent and first order. FIG. 13 is an Ahhrenius plot of the solubilization rate constant that shows the energy barrier to solubilization is high, $E^{??}_a = 460$ kJ mol$^{-1}$.

The microstructural form into which phospholipids self-assembly does not appear to influence the kinetics of detergent solubilization. Egg PC vesicles also show first order kinetics (Mimms, et al., 1981). The rates are very sensitive to the aggregation "state" of the phospholipid, and under these circumstances the right crystalline packing in tubules may be advantageous for slow solubilization of the drug by bile salts and other biological detergents.

V. ADMINISTERING THE COMPOSITE COMPOUNDS

HAR microstructures will be used for the continuous administration of therapeutics to animals and patients. HAR microstructure-based continuous release can be used for administering therapeutics, for example and without limitation, topically, orally, intramuscularly, intranasally, subcutaneously, intraperitoneally, intralesionally, intravenously, or any other administration means now known or hereafter developed that allow for the compounds to remain in HAR lipid microstructures. Moreover, the safety and comfort of the patient also must be considered. Larger diameter HAR microstructues (about 1 µm diameter) are unlikely to be safe for injection into the circulatory system because of possible clogging of capillaries. All other internal and external sites of drug delivery are possible, however. Most of the tubule mass is in the wall. This means that there is a large "wasted" central lumen in the tubules, which reduces the possible drug loading. Multi-bilayer tubules or cochleate cylinders thus may be better suited for circumstances where high drug loading is necessary. Smaller and more flexible tubules and cochleate cylinders have less wasted space and may also be small enough to pass through the capillary beds.

HAR-microstructure-based therapeutic delivery systems can provide controlled release in topical or subcutaneous applications. The relatively long length of some of the microstructures can immobilize them without a rigid polymeric matrix. HAR microstructures also can be used in mucosal and oral delivery. The tight packing of the lipid molecules in the HAR microstructure could afford protection of certain drugs such as peptides from the premature enzymatic hydrolysis that now plagues peptide delivery systems as has been shown for calcium-induced cochleate cylinders. While there are often ample concentrations of proteolytic and lipolytic enzymes present in the interstitial fluid in vivo, these enzymes are often inhibited to prevent uncontrolled cell damage. To ensure that the therapeutic will be enzymatically released from the HAR microstructures in an extracorporeal site, such as in topical applications or in vitro, HAR microstructures could be co-suspended with hydrolytic enzymes.

While there is nothing inherently antigenic about a lipid HAR microstructure, subcutaneous injection of some drug-coated HAR microstructures might be used to induce an inflammatory response, as demonstrated by the adherence of some cells to $DC_{,8,9}PC$ cylinders. The cellular environment in the presence of such a response will provide ample proteolytic enzymes to cleave prodrugs from the HAR microstructure surfaces, which could be an advantage. Some vaccination protocols require repeated dosing with vaccines because a single bolus dose does not raise an adequate immune response. HAR microstructures placed in subcutaneous sites could act as long-acting vaccines that deliver antigen long enough to create a strong immune response. Because the rate of degradation of lipidated drugs will be quite different depending on whether the surfactants are in the form of HAR microstructures or liposomes, it is possible that raising the local temperature above $T_m$, which converts the HAR microstructures to liposomes, could provide a method of greatly increasing the delivery rate from implanted microstructures on demand. Even if the in vivo use of HAR microstructures is restricted for some reason, continuous therapeutic release using HAR microstructure could still be important in such in vitro applications where delivery of some chemical is required over a long period at a constant rate. A biotechnologically important example would be the delivery of growth factors or antibiotics to cells being cultured in containers too small to merit continuous infusion of such factors.

In order to provide steady, continuous therapeutic release, the rate of dissolution or enzymatic cleavage of the therapeutic from the HAR microstructures must be relatively constant. This steady, continuous therapeutic release has been confirmed using a variety of methods.

VI. DOSAGE-RANGE STUDIES IN ANIMALS

Doseage-range finding evaluations of drug delivery compounds made in accordance with the present invention also have been conducted by BIOSUPPORT, INC., Redmond, Wash. Male Balb C mice, 18–22 grams, 3–12 months, were used for the study. Balb C mice were selected because they (1) historically have been used for such test and (2) are a reliable indicator for assessing potential drug toxicity.

The compound tested was Pro$_3$-glutamic acid didodecylamide, and was administered to the animals in an aqueous solution comprising 120 nM NaCl at a pH of 7.2. The control for the study was 120 mM NaCl at a pH of 7.2.

13 mice were used, divided into three groups (1 group of three animals, and 2 groups of 5 animals). The rear flanks of the animals were shaved prior to receiving injections. The group 1 animals received a single 250 microliter injection of the control, and were euthanised at 15 days. The group two and three animals received a single 250 microliter control injection at a first site, and a 250 microliter injection, 100 micrograms of the test material, at a second site. The group two animals were euthanised at eight days, and the group three animals were euthanised at 15 days. The health of the animals was monitored daily.

Histology analysis was performed on tissue collected from the injection sites and preserved in 10% neutral buffered formalin solution. Cross sections from skin injection sites and surrounding tissue were procesed by normal paraffin embedding and staining by Hematoxylin and Eosin.

The health of the 13 animals in the study were normal throughout the study, and there were no consistent changes in body weight throughout the study. Histopatholigcal evaluation showed mild incidence of dermatitis, folliculitis and perifolliculitis. However, these effects likely were the result of trauma caused by shaving or injection, and not some negative reaction to the injected materials. The study indicated that there was no gross toxicity associated with the tested material.

VII. EXAMPLES

The following examples are provided to illustrate particular features of the present invention. The examples should not be construed to limit the scope of the invention to the specific aspects described.

Example 1

This example describes the synthesis of glutamine-based amphiphiles using hexadecylamine to form dihexadecyl glutamides. The synthesis described can generally be used for the synthesis of a variety of compounds wherein the length of the side chains is varied.

In general, the following methods were followed in the synthesis of compounds in accordance with the present invention. All chemicals and solvents from commercial sources were reagent grade. All reactions were carried out under an inert atmosphere, such as an argon atmosphere, with the exception of the acetylation which was done in a manual solid peptide synthesis vessel. All amino acids used were of L-configuration. Thin layer chromatography (TLC) was done using silica ge160 $F_{254}$ from EM Science. The spots were visualized using 0-tolidine, ninhydrin, or both. Flash chromatography was done using silica ge160 (230–400 mesh) also from EM Science. The reported yields represent actual amounts recovered after purification. 1H NMR spectra were recorded on Brucker 200, 300, or 500 MHz. HPLC were done on Rainin Dynamax solvent delivery system or Perkin-Elmer Series 400. Mass spectra(ES-MS) were taken on Kratos Profile HV-4 with electrospray ionization source, at the University of Washington mass spectrometer lab. Samples were mixed with 1:1 methanol and water containing 1% acetic acid.

The first step in the synthesis of dihexadecyl glutamides involved forming an activated ester from glutamic acid with the amino group protected with a CBZ protecting group. This allows the activated ester to be coupled with hexadecylamine. In the present example, N-hydroxysuccinimide was used to activate the ester.

5.0 grams of glutamic acid protected with a CBZ protecting group (referred to as Z-glutamic acid) was dissolved in 100 ml of dry THF. 4.64 grams of N-hydroxysuccinimide (1.1 equivalents; 2.2 molar equivalents) were added to the solution, which was then cooled to about 0° C. using an ice/methanol bath. 7.69 grams of 1,3-dicyclohexylcarbodiimide (DCC; 1.05 equivalents) were added, followed by stirring at about 0° C. for 2 hours. The solution was then allowed to warm up slowly with stirring overnight. DCU (dicylohexylurea, which forms as a byproduct of the reaction) was then removed by filtration to give an oily solid. 150 milliliters of ethyl acetate were added to precipitate more DCU, which was then removed by filtration. 50 milliliters of ethyl acetate were then added, and the solution was washed with saturated NaHCO$_3$, brine and water, followed by drying over sodium sulfate. The mixture was then filtered, and concentrated in vacuo. The concentrated product was then tritiated with ethyl ether to provide a white powder corresponding to the di-N-hydroxysuccinimide ester. 300 mHz H$^1$ NMR showed that the product was substantially pure (all structures of the products made according to the present invention were confirmed by 300 mHz H$^1$ NMR.

The di-N-hydroxysuccinimide-Z-glutamic acid ester was then ready for coupling with an amine. 1.0 (0.10 mmoles) gram of the di-N-hydroxysuccinimide-Z-glutamic acid was dissolved in 25 milliliters of chloroform ester. 1.1 equivalents of hexadecylamine (available commercially) were then added to the solution with stirring for about twenty fours. The resulting solution was washed with saturated sodium bicarbonate, brine, and dried over sodium sulfate. Diethyl ether was then added to precipitate a solid. The solid was resuspended in ethyl acetate, and the semi-solid product was filtered, washed (3X) with ether, and dried. The product was purified using a silica gel column, the eluting solution comprising chloroform-5% methanol. This provided compounds comprising the hexadecylamine side chains coupled to the glutamic acid core, but with the CBZ protecting group still intact.

25 grams of the CBZ-protected compound were then dissolved in 2 milliliters of trifluoroacetic acid (TFA). 3 milliliters of 300 HBr were then added. The solution was stirred at room temperature for two hours. The solution was then filtered and washed with acetic acid. The resulting product was then resuspended in ethyl ether and filtered, and then dried in vacuo to produce the bromide salt. The free amine was produced by first dissolving the product in chloroform, and then adding saturated sodium bicarbonate, followed by filtration and drying in vacuo.

In a manner similar to that described above, related compounds have been synthesized by varying the length of the amine side chains. For instance, the same protocol can be used to synthesize the compounds shown above in Table 1 by substituting dodecyl amine and tetradecylamine for hexadecylamine.

Example 2

This example describes coupling a tetrapeptide to a glutamine-based lipid, which can be produced as discussed above in Example 1. A tetrapeptide (boc-glylys-ε-CBZ-sar-pro) was purchased from Anapec of St. Jose, Calif. The tetrapeptide was purified using a silica gel column and a chloroform:methanol:acetic acid (9:1:0.2) elutant system. The product was collected and then extracted with methylene chloride.

70 milligrams of the tetrapeptide (1.05 equivalents) were dissolved in 200 μl of dry N,N-dimethylformamide (DMF). 1.0 equivalent of C-12 glutamine lipid shown in Table, synthesized as stated above, was dissolved in 2.0 milliliters of DMF, and added to the solution containing the tetrapeptide. The resulting solution was cooled to about 0° C. 1.1 equivalents of diethyl phosphorylcyanate were dissolved in about 200 μliters of DMF and then added to the solution, followed by about 1.1 equivalents of triethylamine. The solution was stirred at about 0° C. for about 2 hours, followed by stirring at room temperature for about 48 hours. 75 milliliters of chloroform were then added to the solution, followed by washing with 10% citric acid, 5% sodium bicarbonate, brine and water. The solution was filtered, and concentrated in vacuo. The product was purified using a silica gel column, eluting with chloroform-2.5% methanol.

60 milligrams of the protected tetrapeptidelipid were then dissolved in 800 μl of methylene chloride. The solution was then cooled to about 0° C. 2 milliliters of HCl/dioxane (4 molar) were added to the solution. The solution was kept at 0° C. for about 2 hours. The solution was then concentrated in vacuo. A fraction of the product was purified using an analytical C-4 HPLC column, using acetonitrile/water/0.6% TFA. The product produced was the salt of the amine.

The free amine was liberated by dissolving 45 milligrams of the tetrapeptide-lipid in 1 milliliter methylene chloride, 9 milliliters 30% HBr/acetic acid, followed by stirring at room temperature for 2 hours. The product was then concentrated, followed by lyophilization from water. A fraction of the product was purified using an analytical C-4 HPLC column with acetonitrile/water/0.6% TFA.

In a manner similar to that described in Example 2, additional peptides and single amino acids derivatives, such as proline derivatives, also have been made. For instance, proline with an FMOC protecting group has been coupled to the C-12 glutamine lipid shown in Table 1 using EDC, the water-soluble derivative of DCC).

Example 3

This example concerns the synthesis of cylinder forming molecules having peptide spacers coupled thereto, wherein the spacer incudes an enzyme cleavage site.

Nα-Glycyl-Nω-(2,2,5,7,8-pentamethylchromane-6-sulfonyl)-arginyl-alanyl-glycyl-glycyl-alanyl-alanyl prolyl-prolyl-prolyl-2-chlorotrityl resin was purchased as a custom order from the University of Washington immunology biopolymer facility.

Nα-Glycyl-Nω-(2,2,5,7,8-pentamethylchromane-6-sulfonyl)-arginyl-alanyl-glycyl-glycyl-alanyl-alanyl prolyl-prolyl-prolyl-2-chlorotrityl resin (200 mg) was washed with $CH_2CL_2$ and reacted with acetic anhydride (41.5 ul, 0.44 mmol) and diisopropylethylamine (95.8 ul, 0.55 mmol) in $CH_2CL_2$ for 2 hrs. in a manual solid phase peptide synthesis vessel on a rocker for 2 hrs. The peptide resin was washed with $CH_2CL_2$ three times and dried in vacuo to produce Nα-Acetyl-glycyl-Nω(2,2,5,7,8-pentamethylchromane-6-sulfonyl)-arginyl-alanyl-glycyl-glycyl-alanyl-alanyl-prolyl-prolyl-prolyl-2-chlorotrityl resin. The Kaiser test was negative.

Nα-Acetyl-glycyl-Nω-(2,2,5,7,8-pentamethylchromane-6-sulfonyl)-arginyl-alanyl-glycyl-glycyl-alanyl-alanyl-prolyl-prolyl-prolyl-2-chlorotrityl resin (80 mg) was treated with 1:1:8 acetic acid:trifluoroethanol:$CH_2CL_2$(2 ml) at room temperature for 30 min. After filtration of the cleaved peptide, the resin was retreated with the same cleavage mixture for 30 min. The combined filtrates were evaporated, dissolved in $H_2O$, and dried in Speed-Vac. The residue was purified by Vydac 218TP1010 column using 35% isocratic acetonitrile:$H_2O$ containing 0.06% TFA and 4 ml/min. flow. The product, Nα-Acetyl-glycyl-Nω-(2,2,5,7,8-pentamethylchromane-6-sulfonyl)-arginyl-alanyl-glycyl-glycyl-alanyl-alanyl-prolyl-prolyl-proline, eluted at 30 min. yielded 22.8 mg after lyophilization. $TLC_{butanol:acetic\ acid\ H2O\ (4:2:2)}$: Rf 0.49 ES-MS: $[M+H]^+$ 1159.0 calcd 1159.35, $[M+Na]^+$ 1181.1 calcd 1181.34, $[M+H+K+]^{2+}$ 599.3 calcd 599.05.

α,γ-ditetradecyl glutamide, synthesized as stated above, in $CHCL_3$ (500 ul) was added to a solution comprising DMF (400 microliters) and Nα-acetyl-glycyl Nω-(2,2,5,7,8-pentamethylchromane-6-sulfonyl)-arginylalanyl-glycyl-alanyl-alanyl-prolyl-prolyl-proline (10 mg, 8.63 umol). The resulting mixture was cooled to 0° C. Diethylphosphorocyanidate (1.55 mg, 9.50 umol) in DMF (15 ul) followed by triethylamine (1.32 ul, 9.50 umol) in DMF (15 ul) were added and the mixture stirred at 0° C. and allowed to warm up to room temperature slowly. 48 hrs. later, the reaction mixture was diluted with $CHCL_3$ and washed with sat'd $NH_4CL$, $H_2O$, sat'd $NaHCO_3$, $H_2O$, brine, dried under $Na_2SO_4$, filtered, evaporated, and dried in vacuo. The product, α,γ-ditetradecyl Nα-acetyl-glycyl-N ω-(2,2,5,7,8-pentamethylchromane-6-sulfonyl)-arginyl-alanyl-glycyl-glycylalanyl-alanyl-prolyl-prolyl-prolyl-glutamide, was further purified by silica gel flash chromatography with $CHCL_3$:MeOH (14–20%) to give 57%. $TLC_{CHCL3:MeOH\ (85:15)}$: Rf 0.29.

α,γ-Ditetradecyl Nα-acetyl-clycyl-Nω-(2,2,5,7,8-pentamethylchromane-6-sulfonyl)-arginyl-alany-glycyl-glycyl-alanyl-alanyl-prolyl-prolyl-prolyl-glutamide (7.80 mg, 4.65 umol) was stirred with 95:1 TFA:$H_2O$ (1 ml) for 2 hrs. at room temperature, the solvent evaporated, and dried in vacuo. Ethyl ether was added to the residue and the product was triturated to give white solid. The solid was isolated by decantation, washed with ether several times, and further purified by reverse phase HPLC column Vydac 214TP1010 using methanol:$H_2O$ containing 0.06% and 0.07% TFA, respectively, with 80% to 100% methanol gradient in 30 min. The product (α,γ-Ditetradecyl Nα-acetyl-glycylarginyl-alanyl-glycyl-gylcyl-alanyl-alanyl-prolyl-prolyl-prolyl-glutamide trifluoroacetate), eluting at 92% methanol, was lyophilized from $H_2O$ to give 3.8 mg, 54%. $TLC_{butanol:acetic\ acid:H2O\ (4:1:1)}$: Rf 0.27. ES-MS: $[M+H]^+$ 1412.6 calcd 1412.89, $[M+2H]^{+2}$ 706.9.

Example 4

This example describes the synthesis of radiolabelled materials, particularly α,γ-Dihexadecyl [5-$^3$H] prolyl-prolyl-prolyl-glutamide hydrochloride. To a solution of [5-$^3$H]proline in 1 mM HCL (1 mCi, speicific activity of 15 Ci/mmol), proline (11.50 mg) was added followed by dioxane and NaOH (4.0 mg, 99.9umol). The mixture was cooled to 0° C., di-tert-butyl dicarbonate (24.0 mg, 109.9umol) was added and stirred at room temperature overnight. The reaction mixture was diluted with $H_2O$, washed with hexane, $CH_2CL_2$ added at 0° C., acidified to pH 1 to 2 with 1N HCL, extracted with $CH_2CL_2$, washed with $H_2O$, dried under $Na_2SO_4$, filtered, evaporated, and dried in vacuo to give a 65% yield of Nα-tert-butoxycarbonyl-[5-$^3$H] proline. $TLC_{CHCL3:MeOH\ (9:1)}$: Rf 0.25.

To a solution of α,γ-dihexadecyl prolyl-prolyl-glutamide hydrochloride (48.8 mg, 59.14umol) in $CHCL_3$ (30 ml), Nα-tert-butoxycarbonyl-[5-$^3$H] proline (14.0 mg, 65.06 umol) was added followed by hydroxybenzotriazole (8.8 mg, 65.06 umol). The mixture was cooled to 0° C. and 1-(3-dimethylarninopropyl)-3-ethylcarbodiimide hydrochloride (12.47 mg, 65.06 umol) followed by diisopropylethylamine were added, and stirred for 45 min at 0° C. before allowing it to warm up to room temperature overnight. The reaction mixture was diluted with $CHCL_3$ and washed with sat'd $NH_4CL$, $H_2O$, sat'd $NaHCO_3$, $H_2O$, brine, dried over $Na_2SO$, filtered, evaporated, and further purified by silica gel flash chromatography with $CHCL_3$:MeOH (97.5:2.5): to give a 93% yiedl of α,γ-Dihexadecyl Nα-tert-butoxycarbonyl-[5-$^3$H]prolyl-prolyl-prolyl-glutamide. $TLC_{CHCL3:MeOH\ (9:1)}$: Rf 0.49.

α,γ-Dihexadecyl Nα-tert-butoxycarbonyl-[5-$^3$H]prolyl-prolyl-prolyl-glutamide was deprotected by dissolving in dichloromethane, followed by addition of 4M HCl/dioxane. The mixture was stirred for 2 hours, the solvent evaporzted and the product purified to provide 100% yield of α,γ-dihexadecyl [5-$^3$H]prolyl-prolyl-prolyl-glutamide hydrochloride. $TLC_{bulanol:acetic\ acid:H2O\ (4:1:1)}$: Rf 0.43. Cospotting, this material with the unlabeled compound on TLC plate showed a single co-migrating spot.

Fluorophores and tritiated acetyl groups can be coupled to the terminal amino group of polypeptides bound to molecules capable of forming cylindrical lipid microstructures. This allows the detection of therapeutics, such as polypeptides, once they have been released from the cylindrical microstructure. One example of a suitable fluorophore is O-aminobenzoic acid. The O-aminobenzoic acid first was protected with a BOC protecting group using known chemistry to produce BOC-aminobenzoic acid. This protected fluorophore was then coupled to the tetrapeptide derivative as produced in Example 2 using EDC. Likewise, a tritiated acetyl derivative can be made by reacting the terminal amino group of the tetrapeptide with tritiated acetic anhydride.

Example 5

This example describes the synthesis of ceramide derivatives made from sphingosine.

The following chemicals were purchased from Sigma-Aldrich and used as received: N-hydroxy succinimide, triphenylmethyl chloride, N,N-dimethyl-4-aminopyridine, benzoyl chloride, anhydrous dimethylformamide, anhydrous acetonitrile, imidazole, t-butylchlorodiphenylsilane, ethylenediaminetetraacetic acid, lithium aluminum hydride, calcium hydride and 1.0 M n-butylammonium fluoride in THF, acetic anhydride, ceramides type III: from bovine brain, galactocerebrosides: type I from bovine brain, galactocerebrosides: type II from bovine brain, N-stearoyl cerebroside, N-palmitoyl cerebroside, N-oleoyl cerebroside, N-nervonoyl cerebroside, psychosine, N-hexanoyl-D-sphingosine, N-palmitoyl-D-sphingosine, N-stearoyl-D-sphingosine, and N-oleoyl-D-sphingosine, N-acetyl-L-glycine, N-t-butylcarbamate-L-proline, nervonic acid.

Dicyclohexylcarbodiimide was purchased from Fluka Chemical and used as received.

The following chemical was purchased from JT Baker and used as received: p-toluenesulfonic acid monohydrate, phosphorous pentoxide, triethylamine, and potassium hydroxide.

$^1$H NMR spectra were obtained in $CDCl_3$ using a Bruker 200 (200 MHz), 300 (300 MHz), or 499 (499 MHz) NMR spectrometer with tetramethylsilane as an internal standard. Tetrahydrofuran was distilled over lithium aluminum hydride prior to use. Ethyl acetate was distilled over calcium hydride. Methylene chloride was distilled over phosphorous pentoxide. Pyridine was distilled over potassium hydroxide.

Silica gel (EM Science Silica Gel 60, 230–400 Mesh) was used for all flash chromatography. Phase contrast optical micrographs were taken using a Zeiss ICM 405 (Carl Zeiss, Inc., Thornwood, N.Y.) with 40x (NA 0.75) or 63x (NA 1.4, oil) phase contrast lenses. Sonication was performed using a bath sonicator (Laboratory Supplies & Co., Inc., Hicksville, N.Y., output 80 KC).

Sphingosine

Mixed N-acyl ceramide (0.250 g) was refluxed for 24 h in 45 mL concd KOH/MeOH and 5 mL $H_2O$. The reaction mixture was cooled to room temp and extracted with 6×25 mL $Et_2O$. Flash chromatography (1:0:0-90:10:1 $CHCl_3$:MeOH:$NH_4OH$) yielded sphingosine as a white solid. The purified residue was dissolved in 50 mL $Et_2O$ and washed with 15 mL 20 mM pH 9.5 EDTA (aq) and with 3×15 mL $H_2O$ and then dried under vacuum (0.068 g, 54%): $R_f$(MeOH) 0.15; $^1$H NMR (300 MHz) 5.77 (m, 1H, C-5), 5.48 (dd, 1H, C-4, J=7.2, 15.4), 4.05 (t, 1H, C-3, J=6.1), 3.65 (octet, 2H, C-1), 2.88 (m, 1H, C-2), 2.06 (q, 2H, C-6), 0.88 (t, 3H, C-18).

N-hydroxy succinimide ester of nervonic acid

Nervonic acid (0.558 g, 1.52 mmol) and N-hydroxy succinimide (0.175 g, 1.52 mmol in 60 mL anhyd EtOAc was stirred overnight with dicyclohexylcarbodiimide (0.314 g, 1.52 mmol). The white precipitate was removed and the supernatant evaporated in vacuo. The residue was recrystallized from EtOH to provide N-hydroxy succinimide ester of nervonic acid as fine white needles (0.539 g, 76%): mp 58°–600 ° C.; $R_f$($CHCl_3$) 0.24; $^1$H NMR (499 MHz) 5.35 (t, 2H, C-15, C-16, J=5.0 Hz), 2.81 (d, 4H, succinimide, J=4.5 Hz), 2.60 (t, 2H, C-2, J=7.6 Hz), 2.01 (m, 4H, C-14, C-17), 1.74 (t, 3H, C-3, J=5.55 Hz), 0.88 (t, 3H, C-24, J=7.0 Hz).

N-nervonoyl ceramide

N-hydroxy succinimide ester of nervonic acid (0.092 g, 198.4 μmol) and sphingosine (0.062 g, 207.0 μmmol) were dissolved in 10 mL anhyd THF and stirred overnight under Ar. Flash chromatography (1:0:0-90:10:1 $CHCl_3$:MeOH:$NH_4OH$) provided N-nervonoyl ceramide as a white solid (0.118 g, 91%): $R_f$(9:1 $CHCl_3$:MeOh) 0.47; $^1$H NMR (300 MHz) 6.20 (1H, NH), 5.73 (m, 1H, C-5), 5.49 (dd, 1H, C-4, J=6.3, 15.4 Hz), 5.33 (t, 2H, C-15', C-16', J=4.6 Hz), 4.30 (t, 1H, C-3), 3.91 (m, 2H, C-2, C-1), 3.69 (dd, 1H, C-1, J=3.1, 11.0 Hz), 2.21 (t, 2H, C-2', J=7.4 Hz),2.00 (m, 6H, C-6, C-14', C-17'), 1.60 (t, 2H, C-3', J=7.8 Hz), 0.88 (t, 6H, C-18, C-24', J=6.3 Hz).

N-nervonoyl-1-0-triphenylmethyl ceramide

N-nervonoyl ceramide (0.018 g, 27.8 μmol), triphenylmethyl chloride (0.015 g, 55.5 μmol) and N,N-dimethyl-4-aminopyridine (0.007 g, 55.5 μmol) in 20 mL anhyd toluene was refluxed for 16 h under Ar. The solvent was removed by rotary evaporation and the residue purified by flash chromatography (9:1-1:1 Hexane:EtOAc) to provide N-nervonoyl-1-O-triphenylmethyl ceramide as a white solid (0.018 g, 72%): $R_f$(3:1 Hexane:EtOAc) 0.21; $^1$H NMR (300 MHz) 7.42-7.22 (15H), 6.06 (d, 1H, NH, J=7.9 Hz), 5.63 (m, 1H, C-5), 5.35 (t, 2H, C-15', C-16', J=5.2 Hz), 5.25 (dd, 1H, C-4, J=6.2, 15.5 Hz), 4.18 (m, 1H, C-2), 3.69 (dd, 1H, C-3, J=3.9, 7.8 Hz), 3.32 (m, 2H, C-1), 2.20 (t, 2H, C-2', J=8.1 Hz), 2.00 (m, 4H, C-14', C-17'), 1.91 (m, 2H, C-6), 1.6(m,\4 2H, C-3'), 0.88 (t, 6H, C-18, C-24', J=6.5 Hz)

N-nervonoyl-1-o-triphenylmethyl-3-O-[diphenyl-t-[butylsilyl] ceramide

N-nervonoyl-1-O-triphenylmethyl ceramide (0.108 g, 0.12 mmol), imidazole (0.066 g, 0.97 mmol), and t-butylchlorodiphenylsilane (0.79 mL, 3.03 mmol) was stirred 19.5 h in 25 mL anhyd DMF under Ar. Added 25 mL of $H_2O$ and extraced with 3×15 mL $Et_2O$. Washed the ether layer with 10 mL H₂O and 10 mL satd NaCl (aq). Flash chromatography (15:1-2:1 Hexane:EtOAc and 1 mL triethylamine/100 mL of solvent) provided N-nervonoyl-1-triphenylmethyl-3-O-[diphenyl-t-butylsilyl] ceramide as a white solid (0.090 g, 66%): $R_f$ (3:1 Hexane:EtOAc 0.66; $^1$H NMR (300 MHz) 7.70-7.23 (m, 25H), 5.36-5.25 (m, 5H, NH, C-4, C-5, C-15', C-16'), 4.39 (t, 1H, C-3, J=5.4 Hz), 4.18 (m, 1H, C-2), 3.94 (dd, 1H, C-1, J=5.1, 10.4 Hz), 3.70 (dd, 1H, C-1, J=5.1, 10.4 Hz), 2.00 (m, 4H, C14', C-17'), 1.86 (m, 2H, C-2'), 1.72 (m, 2H, C-6), 1.44 (m, 2H, C-3'), 1.04 (s, 9H, t-Bu), 0.88 (t, 6H, C-18, C24', J=7.3 Hz).

N-nervonoyl-3-O-[diphenyl-t-butylsilyl] ceramide

N-nervonoyl-1-0-triphenylmethyl-3-O-[diphenyl-t-butylsilyl] ceramide (0.093 g, 82.4 μmol) was stirred for 4 h with p-toluenesulfonic acid monohydrate (0.010 g, 49.4 μmol) in 20 mL 1:1 MeOH:CH₂Cl₂. Added Et₂O (40 mL) and washed the solution with 10 mL 5% NaHCO₃ (aq) and 10 mL H₂O. Flash chromatography (6:1-0:1 Hexane:EtOAc) provided N-nervonoyl-3-O-[diphenyl-t-butylsilyl] ceramide as a white solid (0.034 g, 47%): $R_f$(3:1 Hexane:EtOAc) 0.15; $^1$H NMR (499 MHz)7.67-7.30 (m, 10H), 5.93 (d, 1H, NH, J=7.1 Hz), 5.42-5.33 (m, 4H, C-4, C-5, C-15', C-16'), 4.34 (t, 1H, C-3, J=4.5 Hz), 3.97-3.82 (m, 2H, C-1, C-2), 3.60 (m, 1H, C-1), 3.14 (m, 1H, OH), 1.98 (m, 6H, C-2', C-14', C-17'), 1.86 (m, 2H, C-6), 1.55 (m, 2H, C-3'), 1.07 (s, 9H, t-Bu), 0.88 (t, 6H, C-18, C-24', J=7.0 Hz).

N-nervonoyl-1-O-(N-acetyl-glycine)-3-O-[diphenyl-t-butylsilyl] ceramide

N-nervonoyl-3-O-[diphenyl-t-butylsilyl] ceramide (0.021 g, 2.37 μmol), N-acetyl-glycine (0.006 g, 47.4 μmol), and N,N-dimethyl-4-aminopyridine (0.06 g, 47.4 μmol) in 21 mL 2:5 CH₃CN:CH₂Cl₂ (anhyd) was stirred for 2 h under Ar whereupon dicyclohexylcarbodiimide (0.010 g, 47.4 μmol) was added and the reaction stirred for 24 h under Argon. The solvent was removed in vacuo. Flash chromatography (5:1-0:1 Hexane:EtOAc) of the residue provided N-nervonoyl-1-O-(N-acetyl-glycvine)-3-O-[diphenyl-t-butylsilyl] ceramide as a white solid (0.016 g, 70%): $R_f$(1:1 Hexane:EtOAc) 0.23; $^1$H NMR (300 MHz) 7.67-7.57 (dd, 4H), 7.46-7.33 (m, 6H),6.09 (bs, 1H, NH), 5.51-5.29 (m, 4H, C-4, C-5, C-15', C-16'), 4.40 (dd, 1H, C-3, J=2.9, 10.8 Hz), 4.26 (bs, 2H, C-1), 4.12 (m, 1H, C-2), 3.93 (t, 2H, glycine, J=111.3 Hz), 2.00 (s, 3H, NAc), 1.05 (s, 9H, t-Bu), 0.88 (t, 6H, C-18, C-24', J=6.4 Hz).

N-nervonoyl-1-O-(N-acetyl-L-proline)-3-O-[diphenyl-t-butylsilyll] ceramide

N-nervonoyl-3-O-[diphenyl-t-butylsilyl] ceramide (0.034 g, 38.4 μmol), N-acetyl-L-proline (0.010 g, 63.6 μmol), and N,N-dimethyl-4-aminopyridine (0.011 g, 90.0 μmol) in 15 mL 1:2 CH,CN:CH₂Cl₂ (anhyd) was stirred for 30 min under Ar. Dicyclohexylcarbodiimide (0.012 g, 57.5 μmol) was added and the reaction stirred for 24 h under Argon. The white precipitate was removed by vacuum filtration and the solvent evaporated in vacuo. Flash chromatography (6:1-0:1 Hexane:EtOAc) of the residue provided N-nervonoyl-1-O-(N-acetyl-L-proline)-3-O-[diphenyl-t-butylsilyl] ceramide as a white solid (0.029 g, 74%): $R_f$(1:1 Hexane:EtOAc) 0.29; $^1$H NMR (300 MHz) 7.68-7.59 (dd, 4H), 7.43-7.26 (m, 6H), 6.14 (d, 1H, NH, J=8.8 Hz), 5.41-5.29 (m, 3H, C-4, C-15', C-16'), 5.14 (dt, 1H, C-5, J=4.0, 8.8 Hz), 4.69 (d, 1H, a, J=7.7 Hz), 4.39 (dd, 1H, C-3, J=3.6, 8.1 Hz), 4.27 (d, 2H, C1, J=12.4 Hz), 4.02 (t, 1H, C-2, J=7.3 Hz), 3.44 (t, 2H, d, J=6.4 Hz), 2.16 (m, 2H, b), 2.02-1.91 (m, 13H, C-6, C-2', C-14', C-17', c, NAc), 1.49 (m, 2H, C-3'), 1.03 (s, 9H, t-Bu), 0.88 (t, 6H, C-18, C-24', J=6.6 Hz).

N-nervonoyl-1-O-(N-t-butylcarbamate-L-proline)-3-O-[diphenyl-t-butylsilyll] ceramide N-nervonoyl-3-O-[diphenyl-t-butylsilyl] ceramide (0.041 g, 46.2 μmol), N-t-butylcarbamate-L-proline (0.011 g, 50.9 μmol) and N,N-dimethyl-4-aminopyridine (0.006 g, 50.9 μmol) was stirred for 4 h under Ar in 7 mL anhyd Ch₃CN and 17 mL anhyd CH₂Cl₂. Dicyclohexylcarbodiimide (0.010 g, 50.9 μmol) was added and the reaction stirred for 24 h under Argon. The white precipitate was removed by vacuum filtration and the solvent evaporated in vacuo. Flash chromatography (7:1-0:1 Hexane:EtOAc) of the residue provided N-nervonoyl-1-O-(N-t-butylcarbamade-L-proline)-3-O-[diphenyl-t-butylsilyl] ceramide as a white solid (0.014 g, 28%): $R^f$(3:1 Hexane:EtOAc) 0.44; $^1$H NMR (300 MHz) 7.67-7.60 (m, 4H), 7.44 -7.26 (m, 6H), 6.02 (d, 1H, NH, J=9.3 Hz), 5.40-5.24 (m, 3H, C-4, C-15', C-16'), 5.06 (dt, 1H, C-5, J=4.0, 8.8 Hz), 4.62 (dd, 1H, a, J=3.7, 6.7 Hz), 4.41-4.10 (m, 4H, C-1, C-2, C-3), 3.46 (m, 2H, d), 1.41 (s, 9H, Ot-Bu), 1.03 (s, 9H, Sit-Bu), 0.88 (t, 6H, C-18, C-24', J=6.2 Hz).

1-O-(N-acetyl-glycine)-nervonoyl ceramide

N-nervonoyl-1-O-(N-acetyl-glycine)-3-O-[diphenyl-t-butyl-silyl] ceramide (0.009 g, 9.1 μmol) in 10 mL anhyd THF and 0,01 mL 1.0M n-butylammonium fluoride (in THF) was stirred for 1 h under Argon. The solvent was removed by rotary evaporation and the residue purified by flash chromatography (2:1-0:1 Hexane:EtOAc) to provide 1-O-(N-acetyl-glycine)nervonoyl-ceramide as a white solid (0.002 g, 29%): $R_f$(EtOAc) 0.25; $^1$H NMR (499 MHz) 6.11 (bs, 1H, NH), 6.01 (bs, 1H, NH), 5.76 (dt, 1H, C-5, J=6.7, 15.5), 5.48 (dd, 1H, C-4, J=6.2, 15.5 Hz), 5.33 (t, 2H, C-15', C-16', J=5.0 Hz), 4.33 (d, 2H, gly), 4.15 (m, 2H, C-2, C-3), 4.00 (m, 2H, C-1), 2.17 (t, 2H, C-2', J=4 Hz), 2.03 (s, 3H, NAc), 0.86 (t, 6H, C-18, C-24', J=6.6 Hz).

1-O-(N-acetyl-L-proline)-nervonoyl ceramide

N-nervonoyl-1-O- (N-acetyl-L-proline)-3-O-[diphenyl-t-butyl-silyl] ceramide (0.021 g, 20.5 μmol) in 12 mL anhyd THF and 0.01 mL 1.0M n-butylammonium fluoride (in THF) was stirred for 2 h under Argon. The solvent was removed by rotary evaporation and the residue purified by flash chromatography (3:1-0:1 Hexane:EtOAc) to provide 1-O-(N-acetyl-L-proline)-ceramide as a white solid (0.011 g, 69%): $R_f$(EtOAc) 0.31; $^1$H NMR (499 MHz) 6.66 (d, 1H, NH, J=7.7 Hz), 5.70 (dt, 1H, C-5, J=6.7, 15.5), 5.47 (dd, 1H, C-4, J=6.2, 15.5 Hz), 5.32 (t, 2H, C-15', C-16', J=4.6 Hz), 4.47-4.26 (m, 4H, a, C-2, C-3), 4.06 (bs, 2H, C-1), 3.64-3.50 (dm, 2H, d), 3.30 (bs, 1H OH), 2.18 (m, 2H, b), 2.07 (s, 3H, NAc), 1.99 (m, 10H, C-6, C-2', C-14', C-17', c), 1.59 (m, 2H, C-3'), 0.86 (t, 6H, C-18, C-24', J=7.0 Hz).

Example 6

This example describes a general HAR microstructure forming regimen. Amphiphile (0.1 mg) was dissolved in anhyd DMF so that the concentration was 1.0 mM. Water was added in ≈10 μL increments until the solution became cloudy. The test tube was then covered and allowed to sit at 20° C. for 2–24 h undisturbed. For larger amounts of amphiphile, water was added with vortex mixing (≈3 sec) between additions.

Example 7

This example describes a general HAR microstructure forming regimen. Amphiphile (0.1 mg) was dissolved in pyridine so that the concentration was 1.0 mM. Water was added in 10 μL increments until the solution became cloudy. The test tube was allowed to sit at 20° C. so that the solvent could evaporate over time.

Example 8

This example describes a general HAR microstructure forming regimen. Amphiphile (0.1 mg) was placed in 1 mL buffered water (10 mM $KH_2PO_4$, 100 mM NaCl, 1.5 mM $NaN_3$, pH=6.6). The solution was thrice incubated for 3 min at 90° C., vortexed for 20 sec and then sonicated for 20 sec. Next, the solution was frozen for 2 min in i-PrOH/$CO_2$(s), thawed rapidly (≈20 sec) and then vortexed 20 sec. The freeze-thaw procedure was repeated three times except that after the last freeze the material was allowed to slowly warm to room temperature over ≈1.5 h.

Example 9

This example describes a general HAR microstructure forming regimen. Amphiphile was placed in ethylene glycol:water (either 19:1 or 1:1 v/v) for a final concentration of 1 mg/mL. The solution was thrice incubated for 10 min at 99° C. m and sonicated at 50° C. (12×30 sec. pulses with 30 sec pauses). After the final sonication the solution was allowed to cool from 99° C. to room temperature over 2.5 h.

Example 10

This example describes a particular HAR microstructure forming regimen. Samples of 0.2 milligrams of $NH_2$-Gly-Lys-Sar-Pro-Glu(NH-$C_{12}H_{25}$)$_2$ or (Pro)$_3$-Glu(NH-$C_{12}H_{25}$)$_2$, were dissolved in 40 µl of MeOH were added to 400 µl of HEPES buffered saline at pH 7.4 while vortexing and incubated for 2 hours at room temperature. In the case of Ac-Gly-Arg-Ala-Gly-Gly(Ala)$_2$-(Pro)$_3$-Glu(NH-$C_{12}H_{29}$)$_2$ (peptide 2), 150 µl of a 1 mg/ml MeOH solution of the peptide lipid was mixed with 350 µl of HEPES buffered saline (HBS), and incubated overnight. Before microscopy the obtained peptide-2 particles were transferred to HBS using centrifugal-driven filtration. To do this, particles were centrifuged on filters with 30,000 Da nominal molecular weight limit (Millipore) for 15 minutes at 30,000 X g at room temperature. After substitution of the filtrate with 1 ml of fresh HBS, centrifugation was repeated. The particles retained on the filter were resuspended in another 200 µl portion of HBS. Optical microscopy of the particles obtained shows that upon dilution of MeOH solution, $NH_2$-Gly-Lys-Sar-Pro-Glu(NH-$C_{12}H_{25}$)$_2$, (Pro)$_3$ Glu(NH-$C_{12}H_{25}$)$_2$, and peptide-2 efficiently form particles with high axial ratios and uniform diameters.

Example 11

This example describes how to make HAR microstructures from Ac-NH-Lys-Ala-Sar-Pro-Glu(NH-$C_{12}H_{25}$)$_2$ and $NH_2$Gly-Lys-Sar-Pro-Glu(NH-$C_{12}H_{25}$)$_2$ by heating and cooling in HBS/EtOH mixtures. 0.2 milligrams of Ac-NH-Lys-Ala-Sar-Pro-Glu(NH-$Cl_{12}H_{25}$)$_2$ and $NH_2$Gly-Lys-Sar-Pro-Glu(NH-$C_{12}H_{25}$)$_2$ were dissolved in 50 µl of EtOH. The minimum fraction of HBS that induces precipitation of the peptide li;ids were found by addition of HBS in 10 ml portions while vortexing, with 5 minute incubations after each addition. These compounds formed cylinders. For Ac-NH-Lys-Ala-Sar-Pro-Glu(NH-$C_{12}H_{25}$)$_2$ the concentration of EtOH in the mixture allowing for precipitation was about 46 percent, by volume, and about 42 percent for $NH_2$Gly-Lys-Sar-Pro-Glu(NH-$C_{12}H_{25}$)$_2$.

Example 12

This example describes forming HAR microstructures by heating and cooling in HBS/MeOH mixtures. 0.1 milligram samples of (Pro)$_3$-Glu-(NH-$C_{14}H_{29}$)$_2$ or (Pro)$_3$-Glu-(NH-$C_{14}H_{29}$)$_2$ dissolved in 20 µl of MeOH each were added to 200 µl of HBS at pH 7.4 while vortexing. Concentrations of MeOH in the samples were adjusted to be between 20 and 50 percent, by volume. Sealed samples were then heated to 65° C., and slowly (within about 4 hours) cooled to room temperature. The obtained particles were separated from MeOH/HBS mixtures by centrifugation at 3000 X g for 15 minutes at room temperature. The obtained pellets were reconstituted in 1 milliliter of HBS. After overnight incubation the particles were filtered on centrifugal-driven filtration units and reconstituted in 150 µl of HBS each. The slow cooling technique resulted in close to 100% conversion of the peptide lipids to particles having high axial ratios.

Example 13

This example describes a stability study to determine the stability of the cylinders at physiological temperatures. Tubules of (Pro)$_3$-Glu(NH-$C_{12}H_{25}$)$_2$ were formed by dilution of MeOH solutions as described above in Example 12. Tubules of (Pro)$_3$-Glu(NH-$C_{16}H_{33}$)$_2$ were formed by heating and cooling in HBS/MeOH mixtures as described above in Example 12. These tubules were then incubated in HBS for 1 hour at 38° C. The results indicate that the stability of the tubules correlates with the $T_M$, i.e., if the $T_M$ is greater than the temperature of the environment, then the tubules are stable. For example, the $T_M$ of (Pro)$_3$-Glu(NH-$C_{16}H_{33}$)$_2$ is about 59° C., and the incubation of these tubules did not convert the tubules to different microstructures. The $T_M$ of tubules of (Pro)$_3$-Glu(NH-$C_{12}H_{25}$)$_2$ is about 29.9° C., and incubation of such tubules at physiological temperature converted the tubules into semi-clear micellar solutions.

EXAMPLE 14

This example describes a stability study of tubules at physiological pH. (Pro)$_3$-Glu(NH-$C_{16}H_{33}$)$_2$ tubules formed by heating and cooling in HBS/MeOH mixtures as described above. Such tubules were then incubated for 45 hours at 40° C. in the presence of fetal calf serum (FCS) or sonicated dioleyoylphosphatidylcholine (DOPC) liposomes in HBS at pH 7.4. Incubation in HBS, which was used as a control, nor the biological fluids tested, did not destroy the tubules. This demonstrates that the presence of lipid membranes and components of blood plasma at physiological temperature are not, by themselves, sufficient to destroy the tubule microstructure. This means that injection of such materials into mammals the morphology of the tubules will not be changed dramatically, and that the tubules will provide natural release in a manner that is characteristic for their shape.

EXAMPLE 15

This example describes the cleavage of a peptide coupled to ditetradecyl glutamide, namely α,γ-Ditetradecyl Nα-acetyl-glycyl-arginyl-alanyl-glycyl-gylcyl-alanyl-alanyl-prolyl-prolyl-prolyl-glutamide trifluoroacetate (substrate). 5.46 nmoles of the substrate in 0.25 molar borate buffer and 1 microliter (0.4 micrograms) trypsin in trypsin buffer were mixed. The mixture was then incubated at 37 degrees C. The course of the reaction was followed by TLC (4:1:1 butanol/acetic acid/water; visualized with O-toluidine). TLC analysis indicated that about 80–90% of cleavage of the peptide by trypsin.

Example 16

This example concerns the enzymatic cleavage of constituent molecules self-assembled into cylinders. A relatively homogeneous population of tubules of $DC_{8,9}PC$ was formed using the techniques stated in *Helical and Tubular Micro-*

*structures Formed by Polymerizable Phosphatidylcholines*, 109:6169–6175 (J. Am. Chem. Soc., 1987). Tubules were precipitated by drop-wise addition of water to a 5 mM solution of the lipid in ethanol until the volume fraction of water reached 70%. The tubules were washed 7 times in distilled/deionized water by repeated centrifugation to remove traces of ethanol. The final pellet of tubules was resuspended in 150 µM NaCl, 50 mM Tris-HCl (pH 8.0) in the presence of 10 mM $CaCl_2$. The tubules were then incubated at 30° C. in Tris-HCl buffer at pH 8.0 at a lipid concentration of 0.5 mM in the presence of 10 mM $Ca^{++}$. At $t_0$, 4 units (2.24 µg/ml) of Naja naja venom $PLA_2$ (Sigma Chemicals) were added to the tubules. At periodic intervals thereafter 100 µl aliquots were removed and quenched with 25 mM EDTA, which scavenges $Ca^{++}$ and stops the $PLA_2$ reaction. The samples were briefly heated to above $T_m$ in a 10-fold excess of TX100 to disperse all tubules, and added to a fluorescence cuvette containing 2.0 ml of 0.2 µM of ADIFAB in calcium-free Tris-HCl buffer. Concentrations of "free" fatty acid were determined from the ratio of intensities and a calibration curve.

Figure 14:
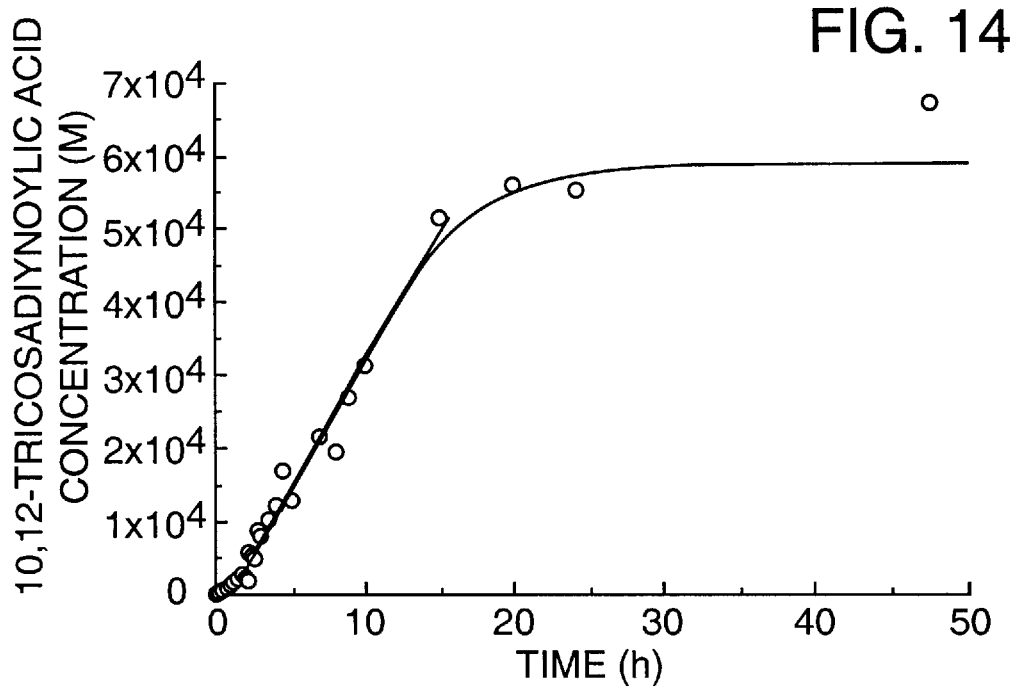
FIG. 14 is a graph showing the total concentration of 10,12-tricosadiynolic acid ($DC_{8,9}PC$) over time following the action of $PLA_2$ on a suspension of $DC_{8,9}PC$.

The results of cleavage by $PLA_2$ are illustrated in FIG. 14. FIG. 14 shows that the hydrolysis rate is substantially constant over the time period tested. The constant rate of hydrolysis continues until nearly all of the substrate is consumed.

Example 17

An in vivo experiment for the delivery of therapeutics is performed as follows. A tritiated polypeptide derivative is prepared by reacting tritiated acetic anhydride with terminal amino group of a polypeptide attached to a cylinder-forming lipid, which was synthesized as stated above. The tritiated derivative is then injected subcutaneously into multiple rabbits. The feces and urine of the test animals is then monitored for the presence of tritiated derivatives. Moreover, at regular intervals, test animals are sacrificed for determining the total presence of tritiated derivatives in tissue samples from the test animals. In this manner, the continuous delivery of therapeutics using the cylindrical lipid microstructures as delivery vehicles is demonstrated.

The present invention has been described in accordance with preferred embodiments. However, it will be understood that certain substitutions and alterations may be made thereto without departing from the spirit and scope of the invention.

We claim:

1. A therapeutic agent comprising a covalent covalent complex according to the formula HARFM-Th, where HARFM is a high axial ratio forming microstructure material selected from the group consisting of tubules, cochleate cylinders, helical ribbons, twisted ribbons, and mixtures thereof the Th being a therapeutic covalently attached to molecules assembled into the high axial ratio microstructure.

2. The therapeutic agent according to claim 1 where the Th is attached to the HARM by a spacer.

3. The therapeutic agent according to claim 2 wherein the spacer is a polypeptide.

4. The therapeutic agent according to claim 3 wherein the polypeptide comprises an enzyme recognition site whereby enzymes can cleave the spacer at the recognition site.

5. The therapeutic agent according to claim 1 wherein the release of therapeutic by the agent follows 0-order kinetics.

6. A method for delivering the covalent complex of claim 1 to an animal or person, comprising administering an effective amount of the covalent complex self-assembled into a high axial ratio microstructure .

7. The therapeutic agent according to claim 1 wherein the therapeutic is a lipid.

8. The therapeutic agent according to claim 1 wherein the high axial ratio forming microstructure material is itself a therapeutic.

9. The therapeutic agent according to claim 1 wherein the therapeutic is selected from the group consisting of nucleic acids, conventional pharmaceuticals and mixtures thereof.

10. A therapeutic agent according to claim 9 wherein the nucleic acid is DNA.

* * * * *